United States Patent
Nelson

(10) Patent No.: US 6,232,326 B1
(45) Date of Patent: May 15, 2001

(54) TREATMENT FOR SCHIZOPHRENIA AND OTHER DOPAMINE SYSTEM DYSFUNCTIONS

(76) Inventor: Jodi A. Nelson, P.O. Box 200231, Denver, CO (US) 80220

(*) Notice: Subject to any disclaimer, the term of this patent is extended or adjusted under 35 U.S.C. 154(b) by 0 days.

(21) Appl. No.: 09/353,490

(22) Filed: Jul. 13, 1999

Related U.S. Application Data

(63) Continuation-in-part of application No. 09/232,311, filed on Jan. 15, 1999, now abandoned.
(60) Provisional application No. 60/092,792, filed on Jul. 14, 1998.

(51) Int. Cl.$^7$ ................................................. A61K 31/44
(52) U.S. Cl. ...................... 514/336; 514/256; 514/275; 514/318; 514/333
(58) Field of Search ................................. 514/256, 275, 514/336, 318, 333

(56) References Cited

U.S. PATENT DOCUMENTS

| | | | |
|---|---|---|---|
| 4,843,086 | 6/1989 | Griss et al. | 514/367 |
| 4,886,812 | 12/1989 | Griss et al. | 514/321 |
| 5,068,325 | 11/1991 | Grell et al. | 514/215 |
| 5,187,162 | 2/1993 | Marangos et al. | 514/46 |
| 5,472,983 | 12/1995 | Flitter et al. | 514/599 |
| 5,508,311 | 4/1996 | Yu et al. | 514/671 |
| 5,585,388 | 12/1996 | Cosford et al. | 514/343 |
| 5,599,991 | 2/1997 | Youdim et al. | 564/308 |
| 5,659,082 | 8/1997 | Flitter et al. | 564/166 |
| 5,688,798 | 11/1997 | Godel et al. | 514/256 |
| 5,736,556 | 4/1998 | Moldt et al. | 514/304 |
| 5,744,500 | 4/1998 | Youdim et al. | 514/647 |
| 5,750,541 | 5/1998 | Bymaster et al. | 514/318 |
| 5,756,548 | 5/1998 | Flitter et al. | 514/616 |
| 5,786,390 | 7/1998 | Youdim et al. | 514/657 |

OTHER PUBLICATIONS

Mytilineou et al., "Deprenyl Protects Dopamine Neurons from the Neurotoxic Effect of 1–Methyl–4–Phenylpyridinium Ion," *J. Neurochem.* (1985) 45(6):1951–53.

Fredriksson et al., "Synergistic interactions between COMT/MAO–inhyibitors and L–Dopa in MPTP–treated mice," *J. Neural Transm. [Gen. Sect.]* (1995) 102:19–34.

Giovanni, A. et al., "Studies on species sensitivity to the dopaminergic neurotoxin 1–methyl–4–phenyl–1,2,3,6–tetrahydropyridine. Part 1: Systemic administration," (1994) *J. Pharmacology and Exp. Therapeutics* 270(3):1000–1007.

Adler, L.E. et al., "Schizophrenia, sensory gating, and nicotinic receptors," (1998) *Schizophrenia Bulletin* 24(2):189–202.

Andrerasen, N.C. et al., "'Cognitive Dysmetria' as an integrative theory of schizophrenia: a dysfunction in cortical–subcortical–cerebellar circuitry?," (1998) *Schizophrenia Bulletin* 24(2):203–218.

Arnauld, E. et al., "Involvement of the caudal striatum in auditory processing: c–fos response to cortical application of picrotoxin and to auditory stimulation," (1996) *Mol. Brain Res.* 41:27–35.

Ballard, P.A. et al., "Permanent human parkinsonism due to 1–methyl–4–phenyl–1,2,3,6–tetrahydropyridine (MPTP): seven cases," (1985) *Neurology* 35:949–956.

Benes, Francine M., "Model generation and testing to probe neural circuitry in the cingulate cortex of postmortem schizophrenic brain," (1998) *Schizophrenia Bulletin* 24(2):219–230.

Breier, A. et al., "Effects of NMDA antagonism on striatal dopamine release in healthy subjects: application of a novel PET approach," (1998) *Synapse* 29:142–147.

Breier, A. et al., "Schizophrenia is associated with elevated amphetamine–induced synaptic dopamine concentrations: evidence from a novel positron emission tomography method," (1997) *Proc. Natl. Acad. Sci. USA* 94(6):2569–2574.

Bunney, B.S. and Grace, A.A., "Acute and chronic haloperidol treatment: Comparison of effects on nigral dopaminergic cell activity," (1978) *Life Sciences* 23:1715–1727.

Burns, R.S. et al., "A primate model of parkinsonism: Selective destruction of dopaminergic neurons in the pars compacta of the substantia nigra by N–methyl–4–phenyl–1, 2,3,6–tetrahydropyridine," (1983) *Proc. Natl. Acad. Sci. USA* 80:4546–4550.

Bymaster, F.P. et al., "Unexpected antipsychotic–like activity with the muscarinic receptor ligand (5R, 6R)6–(3–propylthio–1,2,5–thiadiazol–4–yl)–1–azabicyclo [3.2.1] octane," (1998) *Eur. J. Pharmacol.* 356(2–3):109–119 (abstract only).

Castagnoli, Neal Jr. and Castagnoli, Kay P., "Metabolic bioactivation reactions potentially related to drug toxicities," (1998) *NIDA Monograph* 173:85–105.

Chiodo, L.A. and Bunney, B.S., "Typical and atypical neuroleptics: differential effects of chronic admininistration on the activity of A9 and A10 midgrain dopaminergic neurons," (1983) *J. Neuroscience* 3(8):1607–1619.

Conley, R.R. and Buchanan, R.W., "Evaluation of treatment–resistant schizophrenia," (1997) *Schizophrenia Bulletin* 23(4):663–671.

Csernansky, J.G. and Bardgett, M.E., "Limbic–cortical neuronal damage and the pathophysiology of schizophrenia," (1998) *Schizophrenia Bulletin* 24(2):231–248.

(List continued on next page.)

*Primary Examiner*—Kathleen K. Fonda
(74) *Attorney, Agent, or Firm*—Greenlee, Winner and Sullivan, P.C.

(57) ABSTRACT

Methods and compositions for the treatment of positive and negative symptoms of schizophrenia and tardive dyskinesia are provided. Compositions include 1-methyl-4-phenyl-1,2, 3,6-tetrahydropyridine and its analogs, and/or pyridinium ions thereof, administered in amounts sufficient to reduce dopamine levels in subcortical areas of the brain without causing symptoms of Parkinson's disease. One course of treatment can result in permanent or long-term amelioration of symptoms.

31 Claims, No Drawings

OTHER PUBLICATIONS

Csernansky, J.G. and Grace, A.A., "New models of the pathophysiology of schizophrenia: Editors' introduction," (1998) *Schizophrenia Bulletin* 24(2):185–187.

Dalvi, D. et al., "Characterization of an unexpected product from a monoamine oxidase B generated 2,3–dihydropyridinium species,"(1992) *J. Org. Chem.* 57:7321–7324.

Damask, S.P. et al., "Differential effects of clozapine and haloperidol on dopamine receptor mRNA expression in rat striatum and cortex," (1996) *Mol. Brain Res.* 41:241–249.

DiMonte, D.A. et al., "Astrocytes as the site for bioactivation of neurotoxins," (1996) *NeuroToxicology* 17(3–4):697–703.

DiPorzio, U. and Zuddas, A., "Embryonic dopaminergic neuron transplants in MPTP lesioned mouse striatum," (1992) *Neurochem. Int.* 20S:309S–320S.

DiPorzio, Umberto, "Cellular and molecular biology of developing nigro–striatal dopaminergic neurons," (1978) http://sun01.iigb.na.cnr.it/iigbact/scienctific/diporzio.html.

Dluzen, D.E. et al., "Estrogen alters MPTP–induced neurotoxicity in female mice: effects on striatal dopamine concentrations and release," (1996) *J. Neurochem.* 66(2):658–666.

Egan, M.F. et al., "Treatment of tardive dyskinesia," (1997) *Schizophrenia Bull.* 23(4):583–609.

Elverfors, A. et al., "3–methoxytyramine formation following monoamine oxidase inhibition is a poor index of dendritic dopamine release in the substantia nigra," (1997) *J. Neurochem.* 69:1684–1692.

Feasey–Truger, K.J. et al., "Stimulus–evoked dopamine overflow in the rat nucleus accumbens is decreased following chronic haloperidol administration: an in vivo voltammetric study," (1995) *Neuroscience Letters* 183:91–95.

Feng, M.R. et al., "Determination of two CI–1007 sulfate metabolites in monkey plasma and urine," (1997) *J. Chromatography B*, 693:159–166.

Feng, M.R. et al., "Pharmacokinetics and pharmacodynamics of an investigational antipsychotic agent, CI–1007, in rats and monkeys," (1997) *Pharmaceutical Research*, 14(3):329–336.

Fenton, W.S. et al., "Determinants of medication compliance in schizophrenia: empirical and clinical findings," (1997) *Schizophrenia Bulletin* 23(4):637–651.

Francis, J.W. et al., "Neuroglial responses to the dopaminergic neurotoxicant I–methyl–4–phenyl–1,2,3,6–tetrahydropyridine in mouse striatum," (1995) *Neurotoxicology and Teratology* 17(1):7–12.

Gainetdinov, R.R. et al., "Dopamine transporter is required for in vivo MPTP neurotoxicity: evidence from mice lacking the transporter," (1997) *J. Neurochemistry* 69:1322–1325.

Gainetdinov, R.R. et al., "Increased MPTP neurotoxicity in vesicular monoamine transporter 2 heterozygote knockout mice," (1998) *J. Neurochem.* 30:1973–1978 abstract only.

German, D.C. et al., "1–methyl–4–phenyl–1,2,3,6–tetra–hydropyridine–induced parkinsonian syndrome in *Macaca fascicularis*: Which midbrain dopaminergic neurons are lost?" (1988) *Neuroscience* 24(1):161–174.

Giovanni, A. et al., "Studies on species sensitivity to the dopaminergic neurotoxin 1–methyl–4–phenyl–1,2,3,6–6etrahydrophridine. Part 2. Central administration of 1–methyl–4–phenylpyridinium," (1994) *J. Pharmacology and Exp. Therapeutics* 270(3):1008–1014.

Gray, Jeffrey A., "Integrating Schizophrenia" (1998) *Schizophrenia Bulletin* 24(2):249–266.

Hajós, M. and Greenfield, S.A., "Synaptic connections between pars compacta and pars reticulata neurones: electrophysiological evidence for functional modules within the substantia nigra," (1994) *Brain Res.* 660:216–224.

Hansen, T.E. et al., "Neuroleptic intolerance," (1997) *Schizophrenia Bulletin* 23(4):567–579–582.

Hung, H.C. and Lee, E.H.Y, "What differentiates prototypical, atypical antipsychotics?"(1998) *Free Radical BioMed* (in press).

Hung, Hui–Chuan and Lee, Eminy H.Y., "MPTP produces differential oxidative stress and antioxidative responses in the nigrostriatal and mesolimbic dopaminergic pathways," (1998) *Free Radical Biol. & Med.* 24(1):76–84.

Hung, Hui–Chuan and Lee, Eminy H.Y., "The mesolimbic dopaminergic pathway is more resistant than the nigrostriatal dopaminergic pathway to MPTP and MPP toxicity: role of BDNF gene expression," (1996) *Molecular Brain Res.* 41:16–26.

Itzhak, Yossef and Ali, Syed F., "The neuronal nitric oxide synthase inhibitor, 7–nitroindazole, protects against methamphetamine induced neurotoxicity in vivo," *J. Neurochemistry* (1996).

Javitch, J.A. et al., "Parkinsonism–inducing neurotoxin, N–methyl–4–phenyl–1,2,3,6–tetrahydropyridine: Uptake of the metabolite N–methyl–4–phenylpyridine by dopamine neurons explains selective toxicity," (1985) *Proc. Natl. Acad. Sci. USA* 82:2173–2177.

Kalgutkar, A.S. et al., "Novel 4–(aryloxy)tetrahydropyridine analogs of MPTP as monoamine oxidase A and B substrates," (1994) *J. Med. Chem.* 37:944–949.

Kandel, E.R., "Disorders of Thought: Schizophrenia," *Principles of Neural Science*, 3d Ed. (Eds. E.R Kandel, J.H. Schwartz, T.M. Jessell) Elsevier, New York, Chapter 55, pp. 853–868.

Karreman, M. et al., "Excitatory amino acid receptors in the ventral tegmental area regulate dopamine release in the ventral striatum," (1996) *J. Neurochemistry* 67(2):601–607.

Karreman, Mignon and Moghaddam, Bita, "The prefrontal cortex regulates the basal release of dopamine in the limbic striatum. An effect mediated by ventral tegmental area," (1996) *J. Neurochemistry* 66(2):589–598.

Krueger, M.J. et al., "Mechanism–based inactivation of monoamine oxidases A and B by tetrahydropyridines and dihydropyridines," (1990) *Biochem. J.* 268:219–224.

Lacey, M.G. et al., "Two cell types in rat substantia nigra zona compacta distinguished by membrane properties and the actions of dopamine and opioids," (1989) *J. Neuroscience* 9(4):1233–1241.

Lacey, M.G. et al., "On the potassium conductance increase activated by $GABA_B$ and dopamine $D_2$ receptors in rat substantia nigra neurones," (1988) *J. Physiology* 401:437–453.

Lamensdorf, I. et al., "Effect of long–term treatment with selective monoamine oxidase A and B inhibitors on dopamine release from rat striatum in vivo,"(1996) *J. Neurochemistry* 67(4):1532–1539.

Langston, J.W. et al., "Pargyline prevents MPTP–induced parkinsonism in primates," (1984) *Science* 225:1480–1482.

Lehman, A.F. et al., "Patterns of usual care for schizophrenia: Initial results from the schizophrenia patient outcomes research team (PORT) client survey," (1998) *Schizophrenia Bull.* 24(1):11–20.

Liu, Y. et al., "A cDNA that suppresses MPP+ toxicity encodes a vesicular amine transporter," (1992) *Cell* 70:539–551.

Maret, G. et al., "The MPTP story: MAO activates tetrahydropyridine derivatives to toxins causing parkinsonism," (1990) *Drug Metabolism Reviews* 22(4):291–332.

Mattes, Jeffrey A., "Risperidone: how good is the evidence for efficacy?," (1997) *Schizophrenia Bulletin* 23(1):155–161.

McAllister, K.H., "The competitive NMDA receptor antagonist SDZ 220–581 reverses haloperidol–induced catalepsy in rats," (1996) *Eur. J. Pharmacol.* 314(3)307–311, abstract only.

McQuade, R.D. et al., "In vivo binding to dopamine receptors: a correlate of potential antipsychotic activity," (1992) *Eur. J. Pharmacol.* 215(1):29–34.

Meltzer, L.T. et al., "CI–1007, a dopamine partial agonist and potential antipsychotic agent. II. Neurophysiological and behavioral effects," (1995) *J. Pharmacology and Exp. Therapeutics* 274(2):912–920.

Mitchell, I.J. et al., "Regional changes in 2–deoxyglucose uptake associated with neuroleptic–induced tardive dyskinesia in the Cebus monkey," (1992) *Movement Disorders* 7(1):32–37.

Miyake, H. and Chiueh, C.C., "Effects of MPP+ on the release of serotonin and 5–hydroxyindoleacetic acid from rat striatum in vivo," (1989) *Eur. J. Pharmacology* 166:49–55.

Mytilineou, C. et al., "L–(–)–desmethylselegiline, a metabolite of selegiline [L–(–)–deprenyl], protects mesencephalic dopamine neurons from excitotoxicity in vitro," (1997) *J. Neurochemistry* 68:434–436.

Naiman, N. et al., "Studies on 4–benzyl–1–methyl–1,2,3,6–tetrahydropyridine, a nonneurotoxic analogue of the parkinsonian inducing agent 1–methyl–4–phenyl–1,2,3,6–tetrahydropyridine," (1990) *Chem. Res. Toxicol.* 3:133–138.

Namura, I. et al., "MPP+ (1–methyl–4–phenylpyridine) is a neurotoxin to dopamine–, noripinephrine– and serotonin–containing neurons," (1987) *Eur. J. Pharmacology* 136:31–37.

Nielson, E.B. et al., "NNC–19–1228 and NNC 22–0031, novel neuroleptics with a 'mesolimbic–selective' behavioral profile," (1997) *Psychopharmacology (Berl)* 129(2):168–178 (abstract only).

Nyberg, S. et al., "A PET study of 5–HT$_2$ and D$_2$ dopamine receptor occupancy induced by olanzapine in healthy subjects," (1997), *Neuropsychopharmacology* 16(1):1–7.

O'Donnell, Patricio and Grace, Anthony A., "Dysfunctions in multiple interrelated systems as the neurobiological bases of schizophrenic sympton clusters," (1998) *Schizophrenia Bulletin* 24(2):267–283.

O'Donnell, P. and Grace, A.A., "Different effects of subchronic clozapine and haloperidol on dye–coupling between neurons in the rat striatal complex," (1995) *Neuroscience* 66(4):763–767.

Patterson, T.A. and Schenk, J.O., "Effects of acute and chronic systemic administration of some typical antipsychotic drugs on turnover of dopamine and potassium ion–induced release of dopamine in the striatum of the rat in vivo," (1991) *Neuropharmacology* 30(9):943–952.

Pearlstein, R.D. et al., "Neuroprotective effects of NMDA receptor glycine recognition site antagonism: Dependence on glycine concentrations," (1998) *J. Neurochemistry* 70(5):2012–2019.

Prince, J.A. et al., "Neuroleptic–induced mitochondrial enzyme alterations in the rat brain," (1997) *J. Pharmacology and Exp. Therapeutics* 280(1):261–267.

Przedborski, S. et al., "Role of neuronal nitric oxide in 1–methyl–4–phenyl–1,2,3,6–tetrahydropyridine (MPTP)–induced dopaminergic neurotoxicity," (1996) *Proc. Natl. Acad. Sci. USA* 93:4565–4571.

Pugsley, T.A. et al., "CI–1007, a dopamine partial agonist and potential antipsychotic Agent. I. Neurochemical effects," (1995) *J. Pharmacology and Exp. Therapeutics* 274(2):898–911.

Reith, J. et al., "Enhanced [$^3$H]DOPA and [$^3$H] dopamine turnover in striatum and frontal cortex in vivo linked to glutamate receptor antagonism," (1998) *J. Neurochem.* 70(5):1979–1985.

Ricuarte, G.A. et al., "3,4–Methylenedioxymethamphatamine selectively damages central serotonergic neurons in nonhuman primates," (1988) *J. Am. Med. Assn.* 260:51–55.

Rogers, A. et al., "The meaning and management of neuroleptic medication: A study of patients with a diagnosis of schizophrenia," (1988) *Soc. Sci. Med.* 47(9):1313–1323.

Rollema, H. et al., "MPP+–like neurotoxicity of a pyridinium metabolite derived from haloperidol: In vivo microdialysis and in vitro mitochondrial studies," (1994) *J. Pharmacol. And Exp. Therapeutics* 268(1):380–387.

Rollema, Hans et al., "In vivo intracerebral microdialysis studies in rats of MPP+ analogues and related charged species," (1990) *J. Med. Chem.* 33:2221–2230.

Rosenhan, D.L. and Seligman, M.E.P. (Eds.) *Abnormal Psychology* 3$^{rd}$ ed. (1995) p. 443.

Seeman, P. and Kapur, S., "Clozapine occupies high levels of dopamine D2 receptors," (1997) *Life Sciences* 60(12):207–216.

Seeman, P. et al., "Dopamine D4 receptors elevated in schizophrenia," (1993) *Nature* 365:441–445.

Schwartz, J.C. et al., "Dopamine D3 receptor: basic and clinical aspects," (1993) *Clin. Neuropharmacol* 16(4):295–314 (abstract only).

Shen, Ke–Zhong and Johnson, Steven W., "Presynaptic GABA$_B$ and adenosine A$_1$ receptors regulate synaptic transmission to rate substantia nigra reticulata neurones," (1997) *J. Physiology* 505(1):153–163.

Shibata, M. et al., "Nitric oxide regulates NMDA–induced dopamine release in rat striatum," (1996) *NeuroReport* 7(2):605–608.

Shikimi, T. et al., "Nullification of a positive correlation between urinary levels of alpha 1–microglobulin and ulinastatin by 1–methyl–4–phenyl–1,2,3,6–tetrahydropyridine (MPTP) in mice," (1997) *Psychoneuroendocrinology* 22(4):269–275, abstract only.

Shore, David, "Recent developments in atypical antipsychotic medications," (1998) *Schizophrenia Bull.* 24(1):33.

Simpson, K., "Smoking offsets one illness; substitute sought to aid schizophrenics," (Jan. 2, 1999) *The Denver Post*, pp. 1A and 14A.

Sokoloff, P. et al., "Molecular cloning and characterization of a novel dopamine receptor (D3) as a target for neuroleptics," (1990) *Nature* 347:146–51.

Sramek, J.J. et al., "Initial safety, tolerability, pharmacodynamics, and pharmacokinetics of CI–1007 in patients with schizophrenia," (1998) *Psychopharmacology Bulletin* 34(1):93–99.

Swerdlow, Neal R. and Geyer, Mark A., "Using an animal model of deficient sensorimotor gating to study the pathophysiology and new treatments of schizophrenia," (1998) *Schizophrenia Bulletin* 24(2):285–301.

Takahata, R. and Moghaddam, B., "Glutamatergic regulation of basal and stimulus–activated dopamine release in the prefrontal cortex," (1998) *J. Neurochem.* 71(4):1443–1449.

Thibaut, F. et al., "The dopamine transporter: characterization and physiopathologic implications," (1995) *Encephale* 21(6):445–451, abstract only.

Thiele, G.M. et al., "Long–term ethanol administration alters the degradation of acetaldehyde adducts by liver endothelial cells," (1996) *J. Am. Assn. Study of Liver Diseases* 24(3):643–648, abstract only.

Tipton, K.R. and Singer, T.P., "Advances in our understanding of the mechanisms of the neurotoxicity of MPTP and related compounds," (1993) *J. Neurochemistry* 61(4):1191–1206.

Toyohira, Y. et al., "Down–regulation of the noradrenaline transporter by interferon–α in cultured bovine adrenal medullary cells," (1998) *J. Neurochemistry* 70(4):1441–1447.

Tune, L.E. et al., "Dopamine $D_2$ receptor density estimates in schizophrenia: a postiron emission tomography study with $^{11}$C–N–methylspiperone," (1993) *Psychiatry Res.* 49:219–237.

Usuki, E. et al., "Studies on the conversion of haloperidol and its tetrahydropyridine dehydration product to potentially neurotoxic pyridium metabolites by human liver microsomes," (1996) *Chem. Res. Toxicol.* 9(4):800–806, abstract only.

Waters, C.M. et al., "An immunohistochemical study of the acute and long–term effects of 1–methyl–4–phenyl–1,2,3, 6–tetrahydropyridine in the marmoset," (1987) *Neuroscience* 23(3):1025–1039.

Wright, J.L. et al., "Identification, characterization and pharmacological profile of three metabolities of (R)–(+)–1,2,3, 6–tetrahydro–4–phenyl–1–[(3–phenylcyclohexen–1–yl)methyl]pyridine (CI–1007), a dopamine autoreceptor agonist and potential antipsychotic agent," (1995) *J. Med. Chem.* 38:5007–5014.

Youngster, S.K. et al., "Evalution of the biological activity of several analogs of the dopaminergic neurotoxin 1–methyl–4–phenyl–1,2,3,6–tetrahydropyridine," (1987) *J. Neurochem.* 48(3):929–934.

Youngster, S.K. et al., "Oxidation of analogs of 1–methyl–4–phenyl–1,2,3,6–tetrahydropyridine by monoamine oxidases A and B and the inhibition of monoamine oxidases by the oxidation products," (1989) *J. Neurochem.* 53:1837–1842.

Zuddas, A. et al., "Specific reinnervation of lesioned mouse striatum by grafted mesencephalic dopaminergic neurons," (1990) *Eur. J. Neuroscience* 3:72–85.

"Parkinson's Disease: A Research Planning Workshop," (1998) http://www.ninds.nih.gov/healinfo/disorder/parkinso/pdreport/pdpathog.htm.

The Parkinson's Web, "Parkinson's is a dopamine deficiency disorder," (1998) http://neuro–chief–e.mgh.harvard.edu/parkinsonsweb/main/drugs/agonist2.html.

National Institute of Neurological Disorders and Stroke, "Parkinson's Disease: A Research Planning Workshop. Etiology." (1998) http://www.ninds.nih.govhealinfo/disorder/parkinso/pdreport/pdetiolg.htm.

National Institute of Neurological Disorders and Stroke, "Parkinson's Disease: A Resarch Planning Workshop. Therapy." (1998) http://www.ninds.hih.govhealinfo/disorder/parkinso/pdreport/pdtherapy.htm.

"Schizophrenia", (1996) http://www.nimh.nih.gov.

Mirkin, Gabe, "Glycine and Schizophrenia," (1994) *Am. J. Psychiatry*.

TREATMENT FOR SCHIZOPHRENIA AND OTHER DOPAMINE SYSTEM DYSFUNCTIONS

CROSS-REFERENCE TO RELATED APPLICATION

This application is a continuation-in-part of U.S. application Ser. No. 09/232,311 filed Jan. 15, 1999, now abandoned, which claims priority to U.S. Provisional Application No. 60/092,792 filed Jul. 14, 1998, both of which are fully incorporated herein to the extent not inconsistent herewith.

BACKGROUND OF THE INVENTION

Schizophrenia is a serious disease affecting one percent of the entire global population including about three million Americans. The annual cost of this disorder to the United Sates alone due to loss of employment, hospitalizations, medications, and the like exceeds 60 billion dollars annually and its toll in human suffering is shown by the ten to thirteen percent suicide rate for people who have the disease (American Psychiatric Association Public Information Online [1998] http://www.psych.org). A permanent or long-term cure for this tragic disease would be of tremendous value to the human race.

Schizophrenia appears to be genetically transmitted. Concordance rates of monozygous twins has been shown to be 48 percent while for dizygous twins concordance was only 17 percent. Concordance for offspring having two schizophrenic parents was 46 percent, while for those with only one schizophrenic parent, concordance was 17 percent. The "schizophrenic" environment and being raised by a schizophrenic parent or step-parent also increases the likelihood of this illness manifesting in exposed children. (Rosenhan, D., and Seligman, M. [1995], Abnormal Psychology, 3d. Ed., Norton & Co, NY, p. 443). Finding an effective treatment could also decrease the prognosis of schizophrenia in children being raised by someone who suffers from this illness.

The symptoms of schizophrenia can be grouped into three separate categories. These are (1) positive symptoms related to hallucinations and reality distortion; (2) disorganized symptoms characterized by attentional impairment and thought disorder; and (3) negative symptoms such as apathy and loss of verbal fluency (O'Donnell, P. O. and Grace, A. A. [1998], "Dysfunctions in multiple interrelated systems as the neurobiological bases of schizophrenic symptom clusters," Schizophrenia Bull., 24(2):267–283). A long history of research has demonstrated the efficacy of D2 receptor antagonism in the alleviation of positive and disorganized symptoms (Gray, J. A. [1998], "Integrating schizophrenia," Schizophrenia Bull., 24(2): 249–266). Persistence of negative symptoms often continues, even following neuroleptic treatment (Arndt, S. et al. [1995], "A longitudinal study of symptom dimensions in schizophrenia," Arch. Gen. Psychiatry, 52:352–359). The stability of negative symptoms has been, by some, attributed to the neuroleptic medications themselves (Carpenter, W. T. [1997], "The risk of medication-free research," Schizophrenia Bull., 23(1):11–18).

Dysfunction of the limbic-cortical system may be implicated in all three types of symptoms. Reduced excitory glutamatergic inputs from the hippocampus and other limbic structures to the ventral striatum may be implicated in positive symptoms of psychosis and thought disorganization, and negative symptoms are likely to result from abnormal functioning of frontal lobe structures, e.g. those that receive connections from limbic structures, and/or anatomical irregularities. (Csernansky, J. G. and Bardgett, M. E. [1998], "Limbic-Cortical Neuronal Damage and the Pathophysiology of Schizophrenia," Schizophrenia Bull. 24(2):231–248.)

Excess dopamine production is implicated in schizophrenia. The dopamine hypothesis of schizophrenia associates the disease with increased activity in dopaminergic neurons. Schizophrenic symptoms may be caused by an abnormal dopaminergic state brought about by a primary limbic-cortical lesion and deficits in glutamatergic inputs to the ventral striatum. (Csernansky, J. G. and Bardgett, M. E. [1998], supra.) Radiotracer studies have shown elevated D2 dopamine receptor levels in schizophrenic patients with increases in striatal dopamine receptors sometimes many times increased over normal values. (Seeman, P. et al. [1993], "Dopamine D2 receptors elevated in schizophrenia," Nature, 365:441–445; Tune, L. E. et al. [1993], "Dopamine D2 Receptor Density Estimates in Schizophrenia: A Positron Emission Tomography Study with $^{11}$C-N-Methylspiperone," Psychiatry Research 49:219–237.) Pharmacologically-invoked dopamine release is estimated to be 300% higher than normal levels. (Breier, A. et al. [1997], "Schizophrenia is associated with elevated amphetamine-induced synaptic dopamine concentration: evidence from a novel positron emission tomography method," Proc. Nat'l Acad. Sci., 94(6):2569–2574.) Dopamine projections from the substantia nigra modulate striatal neuronal activity via dopamine D1 and D2 receptors. (Egan et al. [1997], "Treatment of Tardive Dyskinesia," Schizophrenia Bull. 23(4):583–609).

One of the strongest pieces of evidence for a dopamine disturbance in schizophrenia arises from the ability of D2 receptor antagonists to alleviate schizophrenic symptoms.

Effective antipsychotics acting on D2 receptors, including "typical" antipsychotics such as haloperidol and "atypical" antipsychotics such as clozapine, result in disruptions of the dopamine system. Long-term haloperidol treatment reduces the activity of dopamine cells in the substantia nigra. Clozapine reduces the activity of dopamine cells in mesolimbic/mesocortical cells in the ventral tegmental area that projects to the limbic system. (O'Donnell, P. and Grace, A. A. [1998], "Dysfunctions in Multiple Interrelated Systems as the Neurobiological Bases of Schizophrenic Symptom Clusters," Schizophrenia Bull. 24(2):267–284.)

Past research has demonstrated a prominent role for dopamine and D2 receptors in the manifestation of psychosis, progression and complications of this disorder. More recent research has uncovered a multitude of abnormalities of the dopamine system itself and in its relation to other neurotransmitter systems in schizophrenia. A review of these studies will convey a general understanding of other more subtle symptoms involved in schizophrenia which manifest from excessive stimulation of other than D2 dopamine receptors.

The five distinct dopamine receptors have been clustered into two families: the D1-like dopamine receptors consist of the D1 and D5 receptors; and the D2-like dopamine receptors consist of the D2, D3 and D4 receptors, the latter having high affinities for a number of antipsychotic drugs. (Damask, S. P. et al. [1996], "Differential effects of clozapine and haloperidol on dopamine receptor mRNA expression in rat striatum and cortex," Molecular Brain Res. 41:241–249.) D4 receptors have been found to be elevated in schizophrenia. (Seeman, P. et al. [1993], "Dopamine D4 receptors elevated in schizophrenia," Nature 365:441–445.) The "typical" antipsychotics that are highly effective in reducing hallucinations and delusions are selective antagonists of D2 receptors. The "atypical" antipsychotics, to which negative symptoms such as affective flattening, and lack of motivation respond, show affinity for both D1 and D2 receptors. (Swerdlow, Neal R. and Geyer, Mark A., "Using an Animal Model of Deficient Sensorimotor Gating to Study the Pathophysiology and New Treatments of Schizophrenia," Schizophrenia Bulletin 24(2):285–301; Benes, F. M., "Model Generation and Testing to Probe Neural Circuitry in the Cingulate Cortex of Postmortem Schizophrenic Brain," *Schizophrenia Bull.* 24(2):219–230.) The $D_1$ receptor is broadly distributed, while the $D_5$ receptor is restricted to expression in the hippocampus, thalamus and hypothalamus in the rodent. $D_2$, $D_3$ and $D_4$ have high affinities for dopaminergic antagonist drugs. The $D_2$ receptor appears to be expressed in most dopaminoceptive regions of the brain including motor and limbic structures. The $D_3$ and $D_4$ receptors are enriched in subcortical limbic system components. (Damask, S. P. et al., "Differential expression in rat striatum and cortex," [1996] *Molecular Brain Res.* 41:241–249.)

More recent studies have demonstrated the involvement of D1, D3 and D4 receptors as contributing to other symptoms of schizophrenia. For example, D1 receptor antagonism correlates highly (r-0.97) with attenuated response in conditioned avoidance tasks that is a predeterminant of neuroleptic efficacy (McQuade, R. D. et al. [1992], "In vivo binding to dopamine receptors: a correlate of potential antipsychotic activity," *Eur. J Pharmacol.* 215(1):29–34). Also, researchers have demonstrated that D1 receptors located in the caudal portion of the striatum, when agonized, activate one of the strongest functional projections related to the auditory cortex (Arnauld, E. et al. [1996], "Involvement of the caudal striatum in auditory processing: c-fos response to cortical application of picrotoxin and to auditory stimulation," *Molecular Brain Res.* 41:27–35). This may be a contributory source of auditory hallucinations. This sensory-neural pathway has not been fully researched. D3 receptor targeting medications are being evaluated for both their antipsychotic properties (antagonism) and Parkinsonian symptom alleviating (agonism) effects (Sokoloff, P. et al. [1990], "Molecular cloning and characterization of a novel dopamine receptor (D3) as a target for neuroleptics," *Nature* 347:146–151). Finally, D4 receptor antagonism has been demonstrated to restore prepulse inhibition (PPI), a sensory gating mechanism that is deficient in schizophrenia (Swerdlow, N. R. and Geyer, M. A. [1998], "Using an animal model of deficient sensorimotor gating to study the pathophysiology and new treatments of schizophrenia," *Schizophrenia Bull.*, 24(2):285–301). Most medications fail to address all the symptoms that can be alleviated by reducing dopamine availability to all these mid-brain receptor subtypes. Dopamine antagonizing medications such as clozapine in psychosis-controlling doses occupy at least 70% of these receptors, as was demonstrated in a recent radioligand study (Seeman, P. and Kapur, S. [1997], "Clozapine occupies high levels of dopamine D2 receptors," *Life Sciences* 60(12):207–216). To a certain degree, antagonism of all dopamine receptors (except D5 which is much more limited in expression) contributes to restorative effects in function.

Studies of psychotomimetic drugs also indicate a relationship between dopaminergic transmission and the positive symptoms of schizophrenia. For example, amphetamine, an indirect dopamine agonist, has psychotomimetic effects. Gray, J. A. (1998), "Integrating Schizophrenia," *Schizophrenia Bull.* 24(2):249–265. A study of amphetamine-induced dopamine striatal 11c-raclopride binding reduction levels confirmed that patients with schizophrenia had significantly higher binding reductions (−22.3%±2.7 vs.−15.5%±1.8). (Breier, A. et al. [1997], "Schizophrenia is associated with elevated amphetamine-induced synaptic dopamine concentrations: evidence from a novel positron emission tomography method," *Proc. Nat'l. Acad. Sci.* USA 94(6):2569–2574).

N-methyl-d-aspartate (NMDA) antagonists such as phenylcyclidine (PCP), also known as "angel dust," and ketamine, induce symptoms resembling schizophrenia. The effective antipsychotic, clozapine, preferentially increases glutamate levels in the prefrontal cortex and reverses behavioral effects of these antagonists, giving rise to the hypothesis that NMDA disturbances are indicated in schizophrenia. Enhanced dopamine may be involved in the effects seen after administration of these NMDA antagonists. Tests show significantly decreased 11c-raclopride binding to dopamine receptors in the striatum after administration of ketamine. (Breier, A. et al. [1998], supra).

There are four main dopaminergic pathways in the mammalian brain: (1) The mesocortical pathway runs from the ventral tegmental part of the mesencephalon to the frontal cortex, and is implicated in schizophrenia. (2) The mesolimbic pathway runs from the mesencephalon to the limbic areas such as the amygdala, hippocampus and nucleus accumbens (Nac) and is also implicated in schizophrenia. Along with the mesocortical pathway, the mesolimbic pathway arises in the ventral tegmental area (VTA) of the mesencephalon. (3) The nigral striatal pathway projects from its cell bodies in the substantia nigra (SN) to the striatum (ST) and is also implicated in schizophrenia (as well as being the one lesioned for the "Parkinson's model in lab animals). The nigral striatal pathway has excessive $D_2/D_3$ receptor sites. (4) The tuberinfundibular tract runs from the hypothalamus to the anterior pituitary and has not been implicated in schizophrenia. It mediates the release of prolactin. (Pies, R. [1997], "What differentiates prototypical atypical antipsychotics?" http://www.mhsource.com.)

Reducing dopamine availability in the mesolimbic and striatal regions via depolarization block (Chiodo et al. [1983], "Typical and atypical neuroleptics: differential effects of chronic administration on the activity of A9 and A10 midbrain dopaminergic neurons," *J. Neuroscience* 3:1607–1619) and receptor antagonism is not inherently compensated for by mesencephalic dopamine receptor upregulations. In a study done by S. P. Damask et al. ([1996], Differential effects of clozapine and haloperidol on dopamine receptor mRNA expression in the rat striatum and cortex," *Molecular Brain Res.* 41:241–249), the up and down regulation of mRNA expression for dopamine receptors was mapped in response to haloperidol and clozapine. This study indicates no evidence of compensatory upregulation of mRNA activity in the basal ganglion. Several areas of the basal ganglia were demonstrated to have a reduction of mRNA activity in response to blockage of receptors and neural firing. Significant increases of dopamine receptor mRNA expression were observed in the cerebral cortex and temporal lobes. This may eventually contribute to the homeostasis of the cortical/subcortical circuitry. It seems there is an inverse reciprocal link between dopamine transmission in the frontal cortex and subcortical areas, especially the nucleus accumbens (Gray, J. A. [1998], "Integrating schizophrenia, *Schizophrenia Bull.*" 24(2):249–266), which has both striatal and limbic components.

Medication non-compliance is present in all forms of illness. It presents one of the most vexing challenges in psychopharmacology (Fenton, W. S. et al. [1997], "Determinants of medication compliance in schizophrenia: empirical and clinical findings," *Schizophrenia Bull.* 23(4):637–65 1). "Non-compliance is seen to create particular medical and social problems when the drugs concerned are neuroleptics (anti-psychotics) such as chlorpromazine or haloperidol" (Rogers, A. et al. [1998], "The meaning and management of neuroleptic medication: A study of patients with a diagnosis of schizophrenia," *Social Science and Medicine* 47(9):1313–1323). There are numerous reasons patients with schizophrenia choose not to comply with a prescribed medication ritual. Between one-quarter and two-thirds of patients cite side effects as their primary reason for medication discontinuance (del Campo, E. J. et al. [1983], "Rehospitalized schizophrenics: what they report about illness, treatment and compliance," *J. of Psychosocial Nurs. and Mental Health Serv.* 21(6):29–33). Other studies have directly linked the severity of psychopathology with non-compliance in both inpatient and outpatient settings (Fenton, W. S. et al. [1997], "Determinants of medication compliance in schizophrenia: empirical and clinical findings," *Schizophrenia Bull.* 23(4):637–651). In a conglomeration of 26 studies using a variety of definitions and detection methods to assess medication use among outpatients, a default rate of 45% was reported (range –10% to 76%) of patients with schizophrenia taking oral medication (Young, J. L. et al. [1986], "Medication noncompliance in schizophrenia: codification and update," *Bull. Am. Acad. of Psychiatry and the Law* 14:105–122). Other studies have shown even higher incidences of non-compliance (up to 55%). In England, where adherence rates for neuroleptics converge at a 50% level, researchers concluded, "This rate of non-consumption of prescribed medications suggests that, for many individuals, non-compliance holds more benefits than compliance" (Rogers et al. [1998], supra, p. 1315). In and outside of the United States the numbers of chronic non-compliant patients remains exceedingly high. Patients who willingly discontinue medications often do not experience full "relapse" until weeks or months following discontinuance, thus they tend not to attribute the relapse to the medication discontinuance (Hertz, M. I. and Melville, C. [1980], "Relapse in schizophrenia," *Am. J. Psychiatry* 137(7):801–805). Non-compliance creates a "revolving door" pattern of relapse and re-hospitalization. This is problematic in that re-hospitalizations are a huge portion of the annual expenditure to treat schizophrenia. Furthermore, inability to achieve long-term symptom stabilization prevents the successful implementation of further rehabilitative measures, described in "The Patient Outcomes Research Teams" (Lehman. A. F. and Steinwachs, D. M. [1998], "Patterns of usual care for schizophrenia: Initial results from the schizophrenia patient outcomes research team (PORT) client survey," *Schizophrenia Bull.* 24(1):11–20).

Conventional treatments for schizophrenia using neuroleptic dopamine receptor antagonists give rise to many side effects, some more severe than the illness itself. (Rogers, A. et al. [1998], "The Meaning and Management of Neuroleptic Medication: A Study of Patients with a Diagnosis of Schizophrenia," *Soc. Sci. Med.* 47(9):1313–1323). The term "neuroleptic" means to "grip" or take control of the neurons, as is evident by the extrapyramidal side effects (EPS) of these drugs, such as seizures, acute dystonia, drug-induced Parkinsonism, akisthisia (inner restlessness and characteristic fidgety movements), tardive dyskinesia (involuntary movements such as chewing, lateral jaw movements, lip smacking and puckering), vermicular writhing and protrusions of the tongue, grimacing, forehead wrinkling, eye blinking and excessive winking and movements of the extremities, and irregular breathing and swallowing, and neuroleptic malignant syndrome (including seizures, dystonia and rigidity, fever, autonomic instability, delirium, myoglobinuria). Additional side effects include sexual dysfunction, urinary problems, hepatic dysfunction, ocular and dermatological problems, and cardiac and respiratory effects. As an example, the neuroleptic haloperidol is quite toxic and gives rise to motor disorders and tardive diskinesias after prolonged periods of administration. (Tarsy, D., and Baldessarini, R. J., In: Shah, N. and Donald, A., eds. *Movement Disorders*, New York: Plenum Press, [1986] pp. 240–243.) Dopamine blocking by the neuroleptic medications results in an excess of prolactin, causing such side effects as decreased sexual interest, anorgasmia, amenhorrea and the like. (Hansen, T. et al. [1977], "Neuroleptic intolerance," *Schizophrenia Bull.* 23(4):567–582.) These side effects have led to the classification of some patients as neuroleptic-intolerant and treatment-resistant schizophrenic patients. (Conley, R. and Buchanan, R. [1997] "Evaluation of Treatment-resistant schizophrenia," *Schizophrenia Bull.* 23(4): 663–674. Such patients have often lost higher cortical functioning to the extent that they are unable to have a sense of spirituality in their lives or pray. Even in patients who are not neuroleptic-intolerant, these severe side effects are a major reason for patient noncompliance with neuroleptic medications (Fenton, W. S. et al. [1997], "Determinants of Medication Compliance in Schizophrenia: Empirical and Clinical Findings," *Schizophrenia Bull.* 23(4):637–651.)

Treatment resistance poses an additional challenge in the lives of people with schizophrenia and health care providers. In a state hospital study, the criteria for resistance were: failure to respond to two six-week drug trials (1,000 mg per day chlorpromazine equivalents), inpatient status of at least four months and at least four months hospitalization required in the preceding five years. It was discovered that 48% (n=803) of Connecticut State Hospital inpatients with a diagnosis of schizophrenia or schizo-affective disorder were treatment resistant (Essock, S. M. et al. [1996], "Clozapine eligibility among state hospital patients," *Schizophrenia Bull.* 722(1):15–25). Other studies have shown that the prevalence of treatment resistance ranges from one-third to one fifth of all patients diagnosed with schizophrenia (Conley, R. R. et al. [1997], "Evaluation of treatment-resistant schizophrenia," *Schizophrenia Bull.* 23(4):663–674). The cost of treatment for this disorder, as previously noted, is extremely high. The cost to care for individuals with treatment resistant forms of this illness is a disproportionately high percentage of the total cost (Revicki, D. A. et al. [1990], "Economic grand rounds: cost effectiveness of clozapine for treatment-resistant schizophrenic patients" *Hospital and Community Psychiatry* 41(8):850–854). This is due to patients being highly symptomatic and often requiring extensive periods of hospital care (McGlashan, T. H. [1990], "A selective review of recent North American long-term follow-up studies on schizophrenia," *Schizophrenia Bull.* 16(4):515–565).

Other therapies used for treatment of positive symptoms of schizophrenia include anti-Parkinson's drugs, anti-depressants, anti-anxiety drugs, and other adjunctive psychosis medications. Compliance by both patients and health care professionals to neuroleptic and other recommended treatment programs is extremely low. (Lehman, A. F. et al. [1998], "Patterns of Usual Care for Schizophrenia: Initial Results from the Schizophrenia Patient Outcomes Research Team (PORT) Client Survey," *Schizophrenia Bull.* 24:(1):11–20.) Physical side effects of medications may leave patients so debilitated that therapy must be provided to teach them to dress themselves, cook and function normally. Methods for adjusting patient dopamine levels are needed which do not lead to the serious side effects of the neuroleptic drugs.

Patients being treated with drugs for schizophrenia are often depressed due to feelings of helplessness and lack of control since they view their circumstances as internally caused, affecting every aspect of their lives, and permanent. Patients receiving medications to reduce dopamine levels are still subject to normal mood swings caused by fluctuations in dopamine levels, and providing a method for such patients to self-regulate their dopamine levels would be desirable in ameliorating depression by giving them feelings of greater control, and a sense that the nature of their condition is specific and temporary rather than global, embracing every aspect of their lives, and permanent.

Tardive Dyskinesia (TD) continues to be a significant clinical problem for both patients and doctors. New atypical neuroleptics were expected to eliminate the development of TD, but currently the condition remains prevalent among patients with long term neuroleptic use. Cumulative five year prevalence rates are 20–26%, ten year prevalence rates are 49%, and 25 year rates are 68%. Dopamine depleters, D1 antagonists, and D2 ligands, which have an antidopaminergic effect in the striatum, are a few methods of treating this neuroleptic induced disorder (Egan, M. F. et al. [1997], "Treatment of tardive dyskinesia," *Schizophrenia Bull.* 23(4):583–609). A study of neural physiological changes in neuroleptic induced TD primates revealed a significant reduction of regional 2-deoxyglucose uptake in the medial segment of the globus pallidus and in the ventral anterior and ventral lateral nuclei of the thalamus in the dyskinetic animals relative to neuroleptic nondyskinetic and controls (Mitchell, I. J. et al. [1992], "Regional changes in 2-deoxyglucose uptake associated with neuroleptic-induced tardive dyskinesia in the Cebus monkey," *Movement Disorders* 7(1):32–37). Some years prior to that discovery, several of the same researchers evaluated MPTP-induced regional 2-deoxyglucose uptake changes. They found there was a dramatic increase of 2-deoxyglucose in the globus pallidus and increased uptake in the ventral lateral nucleus of the thalamus (Mitchell, I. J. et al. [1986], "Neural mechanisms mediating 1-methyl-4-phenyl-1,2,3,6-tetrahydropyridine-induced parkinsonism in the monkey: relative contributions of the striatopallidal and striatonigral pathways as suggested by 2-deoxyglucose uptake," *Neuroscience Letters* 63:61–65). Findings from these studies indicate that MPTP causes an increase in 2-deoxyglucose uptake in the same areas that TD causes a decrease in 2-deoxyglucose uptake.

Hypofunctionality of the frontal and temporal lobes has been observed in numerous PET studies of the schizophrenic brain (Kawasaki, Y. et al. [1992], "Regional cerebral blood flow in patients with schizophrenia: A preliminary report," *Eur. Archives of Psychiatry and Clinical Neuroscience*, 241:195–200; Yurgelun-Todd, D. A. et al. [1996], "Functional magnetic resonance imaging of schizophrenic patients and comparison subjects during word production," *Am. J. Psychiatry* 153:200–205). It is believed that this may be contributory to negative symptoms. Damask et al. reported chronic neuroleptic (clozapine and haloperidol) administration invoked large upregulations of dopamine receptor transcripts in both the frontal and temporal lobes (Damask, S. P. et al. [1996], "Differential effects of clozapine and haloperidol on dopamine receptor mRNA expression in the rat striatum and cortex," *Molecular Brain Res.* 41:241–249).

Studies have demonstrated that the prefrontal cortex regulates the basal release of dopamine in the limbic system, an effect known to be mediated by the ventral tegmental area (VTA) (Karreman, M. and Moghaddam, B. [1996], The prefrontal cortex regulates the basal release of dopamine in the limbic striatum: an effect mediated by ventral tegmental area," *J. Neurochemistry* 66:589–598). Infusion of monoamines, such as dopamine, in the prefrontal cortex has an inhibitory effect on the pyramidal neurons that project to subcortical structures, inhibiting dopamine release in these areas (Sesack, S. R. and Bunney, B. S. [1989], "Pharmacological characterization of the receptor mediating electrophysiological responses to dopamine in the rat medial prefrontal cortex: a microiontophoretic study," *J. Pharmacol. Exp. Ther.* 248:1323–1333). This implies that dopamine release in the subcortical structures is attenuated by increased dopamine availability in the prefrontal cortex. Limbic-cortical and frontal-cortical functional abnormalities have been traced to these structural areas and pathways, resulting in disruption of this neural circuitry (Csernansky, J. G. and Bardgett, M. E. [1998], Limbic-cortical neuronal damage and the pathophysiology of schizophrenia," *Schizophrenia Bull.* 24(2):231–248). Furthermore, blockading the prefrontal cortex (PFC) dopamine receptors with neuroleptic medications in effect prevents the PFC from naturally down-regulating the release of dopamine in the VTA and subsequently into the limbic system.

A similar type of neural metabolic restoration of homeostasis has been observed with hypofrontality caused by Parkinson's Disease. When over-excited midbrain neurons are stereotaxically lesioned by the procedure of posteroventral pallidotomy (PVP), there is a PET scan observable restoration of frontal cortex activity (East, R. [1996], "Victory over Parkinson's," http://xfdm08.aps1.anl.gov/PARKINSON/parkinson_victory.html# What_is_it).

In 1982, MPTP was introduced on the streets of California as a contaminant of a "synthetic heroin." A number of those who took the synthetic heroin in large amounts (4.5 grams in one reported case, 30 grams in a second, 16 ounces in a third, and one teaspoon per day for about a month in a fourth reported case) developed symptoms of severe Parkinson's Disease, but with no change in mental status. Neurotoxic effects appeared limited to damage to the substantia nigra. One individual who had taken low doses of MPTP showed significant destruction of nigrostriatal dopamine neurons; however, this patient had no symptoms of motor deficit or Parkinson's disease. A longitudinal follow-up of these individuals reported they are basically doing well and leading normal lives, albeit requiring daily Parkinsonian medications. There was no evidence of any cognitive deficits or peripheral damage (short- or long-term) due to large systemic exposure of MPTP other than a reported "burning sensation" during and shortly after the injection. (Ballard, P. A. et al. [1985], "Permanent human parkinsonism due to 1-methyl-4-phenyl-1,2,3,6-tetrahydropyridine (MPTP): Seven cases," *Neurology* 35:949–956.)

MPTP has been used as a model to simulate Parkinson's disease in animal models because it selectively destroys the small group of dopaminergic nerve cells in the substantia nigra of the brain which are also destroyed by degenerative processes in naturally-occurring Parkinson's disease. (See, e.g. U.S. Pat. No. 5,599,991.)

MPTP is relatively harmless until converted into its active metabolite MPP+ by monoamine oxidase B (MOA-B). MPTP, as well as being a substrate for MOA-B, is also a mechanism-based inhibitor of this enzyme. (Krueger, M. J. et al. [1990], "Mechanism-based inactivation of monoamine oxidases A and B by tetrahydropyridines and dihydropyridines," *Biochem. J.* 268:219–224.) On exposure to MOA-B it is irreversibly converted into MPP+ and a small amount of MTDP+ is usually also formed (with a lesser degree of toxicity). After an intracranial injection of MPTP, one hundred percent recovery of this substance can be reobtained in its original and metabolite forms. (DiMonte, D. A. et al. [1996], "Astrocytes as the Site for Bioactivation of Neurotoxins," *NeuroToxicology* 17(3–4):697–704.)

Tipton, K. F. and Singer, T. P. (1993), "Advances in our Understanding of the Mechanisms of the Neurotoxicity of MPTP and Related Compounds," *J. Neurochem.* 61(4):1191–1206 is a review article discussing the biochemical actions of MPTP and its selective destruction of nigrostriatal dopaminergic neurons. MPP+ provides its toxic effects by penetrating the mitochondrial matrix where respiratory inhibitor rotenone and piericidin A react. This results in the augmentation of reducing agents from NADH dehydrogenase to reach ubiquinone [coenzyme Q (CoQ)], thus halting the process of oxidative phosphorylation. The necessity for MPP+ to accumulate in sufficiently high concentrations for this chain of events to occur means that most cell types are susceptible only to a transient decrease in ATP production. MPP+ is a substrate for the dopamine transporter mechanism and its high binding affinity to the neuromelanin present in the nigral dopamine neurons renders these neurons most susceptible to MPP+ toxicity.

MPTP is also a substrate and mechanism-based inhibitor of MAO-B (Krueger, M. J. et al. [1990], "Mechanism-based inactivation of monoamine oxidases A and B by tetrahydropyridines and dihydropyridines," *Biochemistry J.* 268:219–224). On exposure to MAO-B, MPTP is irreversibly converted into $MPP^+$ and a small amount of $MTDP^+$ is usually also formed (with a lesser degree of toxicity). After an intracranial injection of MPTP, 100% recovery of this substance can be obtained in is original and metabolite forms (Di Monte, D. A. et al. [1996], "Astrocytes as the site for bioactivation of neurotoxins," *Neurotoxicology* 17:697–704). This is a reliable indicator that no other unwanted reactions are occurring.

In studies evaluating the changes in brain energy production and enzyme levels with the administration of MPTP and neuroleptic medications, fascinating similarities in these compounds emerged. MPTP bears structural and pharmacological similarities to haloperidol, which is 4-[4-(4-chlorophenyl)-4-hydroxy-1-piperidinyl]-1-(4-fluorophenyl)- 1-butanone. Both undergo oxidation, resulting in neurotoxic metabolites $MPP^+$ and $HPP^+$ respectively (Rollema, H. et al. [1994], "$MPP^+$-like neurotoxicity of a pyridinium metabolite derived from haloperidol: In vivo microdialysis and in vitro mitochondrial studies," *J. Pharmacology & Exp. Therapeutics* 268:380–387). MPTP when administered in subtoxic doses was found to cause generalized reduction in NADH, ubiquinone oxidoreductase (complex I) in rat brain, as is seen with both haloperidol and fluphenazine. MPTP was further evaluated alongside the chronic administration of haloperidol, fluphenazine, and clozapine. All potentiate a moderate but generalized increase in monoamine oxidase-A and -B (MAO-A and -B) in the striatum and hippocampus. There existed a strong positive correlation between the hippocampal increase of MAO-A activity and an increase in COX (cytochrome-c oxidase, complex IV) activity, observed in the MPTP, clozapine, and fluphenazine groups. Based upon these results, observable reductions in COX activity in the schizophrenic brain are not the result of neuroleptic treatment, but rather COX is increased as a result of neuroleptic (and ironically MPTP) treatment, particularly in the glutamatergic rich regions of the hippocampus and frontal cortex. It is assumed this may contribute to the therapeutic value of these compounds (Prince, J. A. et al. [1997], "Neuroleptic-induced mitochondrial enzyme alterations in the rat brain," *J Pharmacology and Exp. Therapeutics*, 280:261–267).

MPP+ is also a neurotoxin to norepinephrine- and serotonin-containing neurons. (Namura, I. et al. [1987], "MPP+ (1-methyl-4-phenylpyridine) is a neurotoxin to dopamine-norepinephrine- and serotonin-containing neurons," *Eur. J. Pharmacology* 136:31–37).

Symptoms of Parkinson's are not usually detected until about eighty percent of the dopamine-producing neurons have died. (Harvard Parkinson's Web Page [1998] http://neuro-chief-e-mgh.harvard.edu/parkinsonsweb/Main/Drugs/agonist2.html.) In primate models, it has been shown that dosages of MPTP in the range of 0.66 mg/kg or more are necessary before symptoms of motor dysfunction occur, that higher dosages over a longer period are necessary for severe nerve cell loss, and that considerable reduction of dopamine may occur without the development of clinical evidence of disordered motor function. (Bums, R. S. et al. [1983], "A primate model of parkinsonism: Selective destruction of dopaminergic neurons in the pars compacta of the substantia nigra by N-methyl-4-phenyl-1,2,3,6-tetrahydropyridine," *Proc. Nat'l. Acad. Sci.* 80:4546–4550.) For antipsychotic effects of neuroleptics to occur, it has generally been found necessary to induce about 70–89% $D_2$ receptor blockade. (Nyberg, S. et al. [1997], "A PET Study of 5-$HT_2$ and $D_2$ Dopamine Receptor Occupancy Induced by Olanzapine in Healthy Subjects," *Neuropsychopharmacology* 16(1):1–7.) However, neuroleptic dosages cause dopamine level reductions in much lesser amounts. (Patterson, T. A., and Schenk, J. O. [1991], "Effects of Acute and Chronic Systemic Administration of Some Typical Antipsychotic Drugs on Turnover of Dopamine and Potassium Ion-Induced Release of Dopamine in the Striatum of the Rat In Vivo," *Neuropharmacology* 30(9):943–952.)

MPP+ is accumulated in the dopamine neuronal uptake system and concentrated within dopamine neurons, accounting for their selective destruction. Some destruction of cells involved in norepinephrine and serotonin also occurs. (Javitch, J. A. et al. [1985], "Parkinsonism-inducing neurotoxin, N-methyl-4-phenyl-1,2,3,6-tetrahydropyridine: Uptake of the metabolite N-methyl-4-phenylpyridine by dopamine neurons explains selective toxicity," *Proc. Natl. Acad. Sci.* 82:2172–2177.) The mesolimbic dopaminergic pathway is about twice as resistant as the nigrostriatal dopaminergic pathway to MPTP toxicity. (Hung, H.-C. and Lee, E. H. Y. [1996], "The mesolimbic dopaminergic pathway is more resistant than the nigrostriatal dopaminergic pathway to MPTP and MPP– toxicity: role of BDNF gene expression," *Molecular Brain Res.* 41:16–26; German, D. C. et al. [1988], "1-methyl-4-phenyl-1,2,3,6-tetrahydropyridine-induced Parkinsonian Syndrome in *Macaca Fascilularis*: Which Midbrain Dopaminergic Neurons are Lost," *Neuroscience* 24(1):161–174).

When systemically injected, MPTP easily diffuses across the blood-brain barrier and, due largely to the high concentrations of MOA-B in the walls of capillaries forming the blood-brain barrier, it is quickly converted to MPP+and does not rediffuse back across into systemic circulation. On the other hand, a systemic injection of MPP+ is prevented from crossing the blood-brain barrier to exert neurotoxic effects due to the presence of the inherent quaternary pyridinium ion. (Miyake, H. and Chiueh, C. C. [1989], "Effects of MPP+ on the release of serotonin and 5-hydroxyindoleacetic acid from rat striatum in vivo," *Eur. J. Pharmacology* 166:49–55; Przedborski, S. et al. [1996], "Role of neuronal nitric oxide in 1-methyl-4-phenyl-1,2,3,6-tetrahydropyridine (MPTP)-induced dopaminergic neurotoxicity," *Proc. Natl. Acad. Sci.* 93(10):4565–4571.) Systemic administration of MPTP causes transient decreases in ATP levels in the liver and noradrenaline cells in the heart and adrenal gland. Even so, these cell types do not possess mechanisms to maintain $MPP^+$ at high enough concentrations to cause sustained mitochondrial inhibition.

A cDNA protein transporter mechanism has been isolated and found to provide resistance to MPP+ toxicity. The RNA expression of this protective protein mechanism has been isolated in both the adrenal gland and monoaminergic cells of the brainstem. Also, the uptake of $MPP^+$ by adrenal medullary chromaffin granules protects the mitochondria in these areas from exposure to the $MPP^+$ generated oxidative phosphorylation inhibitor. Inhibition of monoamine oxidase prevents MPTP toxicity, and the monoamine oxidase inhibitor deprenyl slows progression of idiopathic Parkinson's Disease. (Liu, Y. [1992], "A cDNA That Suppresses MPP+ Toxicity Encodes a Vesicular Amine Transporter," *Cell* 70:539–551.) 7-Nitroindazole (7-NI) also protects MPTP-injected mice against nigrostriatal dopaminergic pathway damage. (Przedborski, S. et al. [1996], "Role of neuronal nitric oxide in 1-methyl-4-phenyl-1,2,3,6-tetrahydropyridine (MPTP)-induced dopaminergic neurotoxicity," *Proc. Natl. Acad. Sci.* 93(10):4565–4571.)

MPTP has been found to cause generalized reduction in NADH:ubiquinone oxidoreductase in rat brain, increase in activity of cytochrome-c oxidase and changes in activities of monoamine oxidase-A and -B, (MAO-A and -B) similar to haloperidol, which is 4-[4-(4-chlorophenyl)-4-hydroxy-1-piperidinyl]-1-(4-fluorophenyl)-1-butanone (Prince, J. A. et al. [1997], "Neuroleptic-Induced Mitochondrial Enzyme Alterations in the Rat Brain," *J. Pharmacology and Exp. Therapeutics*, 280:261–267.) Agents which block MAO-B activity prevent neurons from damage by MPTP and similar neurotoxins. (U.S. Pat. No. 5,508,311.) Deprenyl and its metabolite desmethylsegiline are such protective agents. (Mytilineau, C. et al. [1997], "L-(–)-Desmethylselegiline, a Metabolite of Selegine [L-(–)-Deprenyl], Protects Mesencephalic Dopamine Neurons from Excitotoxicity in Vitro," *J. Neurochemistry* 68(1):434–436.)

Gonadotrophic hormones, especially estrogen, have been shown to function as neural protective chemicals for dopamine neurons. They not only protect dopamine neurons from MPTP toxicity, but increase dopamine release and upregulate receptor transcripts. (Dluzen, D. E. et al. [1996], "Estrogen Alters MPTP-Induced Neurotoxicity in Female Mice: Effects on Striatal Dopamine Concentrations and Release," *J. Neurochem.* 66(2):658–666.)

Neural protective agents for other types of neurons include desipramine, which blocks the reuptake of norepinephrine (NE) a thousand times more effectively in the cortical areas than the corpus striatum, making it superior to mazidol which also provides some protective blocking, and citalopram, which prevents serotonin reuptake and also preserves the serotonin or indolamine neurons exposed to MPP+ from degeneration. (Javitch, J. A. et al. [1985], supra.) L-Dopa augments dopamine following MPTP administration. (Yang et al. [1986], "Depletion of glutathione in brainstem of mice caused by N-methyl-4-phenyl-1,2,3,6-tetrahydropyridine is prevented by antioxidant pretreatment," *Neuroscience Letters* 63:56–60.) Guanethidine, a sympatholytic agent, 10 mg/kg, given s.c. once daily three days prior to systemic MPTP injections in rats, prevents peripheral catecholamine release by MPTP and/or $MPP^+$ without interrupting desired effects of dopamine cell attenuation. (Giovanni, A. et al. [1994a], "Studies on species sensitivity to the dopaminergic neurotoxin 1-methyl-4-phenyl-1,2,3,6-tetrahydropyridine. Part 1: Systemic administration," *J. Pharmacology and Exp. Therapeutics* 270:1000–1007).

There are marked species differences in susceptibility to the neurotoxic effects of MPTP. Humans, non-human primates and mice are sensitive to MPTP, whereas rats are relatively insensitive to its effects. (Giovanni, A. et al. [1994], "Studies on Species Sensitivity to the Dopaminergic Neurotoxin 1-Methyl-4-Phenyl-1,2,3,6-Tetrahydropyridine. Part 2. Central Administration of 1-Methyl-4-Phenylpyridinium," *J. Pharmacology and Exp. Therapeutics* 270:1008–1014.) Certain strains of mice (i.e. the Black C57 or C57B1) appear susceptible to MPP+, whereas other species of mice and rats are not. Age is also a factor in MPTP-induced dopamine cell loss, with older animals appearing more sensitive to neural toxicity. Parkinson's disease also generally has a relatively late onset. In a study undertaken with rhesus monkeys, motor effects were first observed after dosages of 0.66 mg/kg, while lesser dosages, e.g. about 0.275 to 0.44 mg/kg, markedly decreased dopamine levels. (Burns, R. S. et al. [1983], "A primate model of parkinsonism: Selective destruction of dopaminergic neurons in the pars compacta of the substantia nigra by N-methyl-4-phenyl-1,2,3,6-tetrahydropyridine," *Proc. Nat'l Acad. Sci.* 80:4546–4550.) In marmosets, behavioral changes and biochemical recovery were observed several months after administration of 1–4 mg/kg of MPTP. (Waters, C. M. et al. [1987], "An Immunohistochemical Study of the Acute and Long-term Effects of 1-methyl-4-phenyl-1,2,3,6-tetrahydropyridine in the Marmoset," *Neuroscience* 23(3):1025–1039.) Humans are five to ten times more sensitive to the neurotoxic effects of MPTM than primates. (Ricuarte, G. A. et al. [1988], "(+/–) 3,4-Methylenedioxymethamphetamine Selectively Damages Central Serotonergic Neurons in Nonhuman Primates," *J. Am. Med. Assn.* 260:51–55.)

A number of analogs of MTPT and $MPP^+$ have been shown to have neurotoxic effects similar to MPTP. (Youngster, S. K. et al. [1989], "Oxidation of Analogs of 1-Methyl-4-Phenyl-1,2,3,6-Tetrahydropyridine by Monoamine Oxidases A and B and the Inhibition of Monoamine Oxidases by the Oxidation Products," *J. Neurochemistry* 53(6):1837–1842; Maret, G. et al. [1990], "The MPTP Story: MAO Activates Tetrahydropyridine Derivatives to Toxins Causing Parkinsonism," *Drug Metabolism Reviews* 22(4):291–332; Rollema, H. et al. [1990], "In Vivo Intracerebral Microdialysis Studies in Rats of MPP+ Analogues and Related Charged Species," *J. Med. Chem.* 33:2221–2230; Naiman, N. et al. [1990], "Studies on 4-Benzyl-1methyl-1,2,3,6-tetrahydropyridine, a Nonneurotoxic Analogue of the Parkinsonian Inducing Agent 1-Methyl-4-phenyl-1,2,3,6-tetrahydropyridine," *Chem. Res. Toxicol.* 3:133–138; Dalvie, D. et al. [1992], "Characterization of an Unexpected Product from a Monoamine Oxidase B Generated 2,3-Dihydropyridinium Species," *J. Org. Chem.* 57:7321–7324; Tipton, K. F. and Singer, T. P., "Advances in Our Understanding of the Mechanisms of the Neurotoxicity of MPTP and Related Compounds," Journal of Neurochemistry 61(4):1191–1206; Castagnoli, Jr., N. and Castagnoli, K. P. [1998] NIH web page http://www.nida.nih.gov.)

Pyridine compounds which have been suggested for use as antipsychotics include C-1007, (R)(+)-1,2,3,6-tetrahydro- 4-phenyl-1[(3-phenylcyclohexen-1-yl)methyl]pyridine (Wright, J. L. et al. [1995], "Identification, characterization and pharmacological profile of three metabolites of (CI1007), a dopamine autoreceptor agonist and potential antipsychotic agent," *J. Med. Chem.* 38:507–5014; Pugsley, T. A. et al. [1995], "I-1007, a Dopamine Partial Agonist and Potential Antipsychotic Agent. I Neurochemical Effects," *J. Pharmacology and Exp. Therapeutics* 274:898–911; Feng, M. R. et al. [1997], "Determination of two CI-1007 sulfate metabolites in monkey plasma and urine," *J. Chromatogr.* B 693:159–166; Meltzer, L. T. et al. [1995], "CI-1007, a Dopamine Partial Agonist and Potential Antipsychotic Agent. II Neurophysiological and Behavioral Effects," *J. Pharmacology and Exp. Therapeutics* 274:912–920; Feng, M. R. et al. [1997], "Pharmacokinetics and Pharmacodynamics of an Investigational Antipsychotic Agent, CI-1007, in Rats and Monkeys," *Pharmaceutical Res.* 14(3):329–336; Sramek, J. J. et al. [1998], "Initial Safety, Tolerability, Pharmacodynamics, and Pharmacokinetics of CI-1007 in Patients with Schizophrenia," *Psychopharmacology Bull.* 34(1):93–99). CI-1007 is not described as a neurotoxin.

U.S. Pat. No. 5,585,388 issued Dec. 17, 1996 to Cosford et al. for "Substituted Pyridines Useful as Modulators of Acetylcholine Receptors" discloses a number of pyridine-based compounds useful as modulators of acetylcholine receptors and said to be useful in the treatment of a wide range of disorders including tardive dyskinesias. No neurotoxic effects of these compounds are disclosed or suggested.

A method for treating schizophrenia which does not cause the serious side effects of neuroleptic drugs is needed. Such a treatment should be permanent, i.e. irreversible, or long-term.

SUMMARY OF THE INVENTION

Approximately one-third of all schizophrenic patients manifest obvious dopamine transmitter and/or receptor increases. Others who do not overtly manifest this abnormality still show improvement of symptoms with the pharmacological blockade of dopamine receptors. These dopamine receptor antagonists ultimately result in overall reductions in dopamine concentrations due to depolarization block and dopamine receptor antagonism. Thus, malfunction of neural circuits, many of which dopamine has a direct and/or indirect role in activating, appears to be involved in schizophrenic symptoms. As has been shown above, blocking dopamine receptors in subcortical areas of the brain substantially reduces schizophrenic symptoms. Generalized reduction of dopamine production in these areas provides similar relief to patients suffering from this disease.

A method is therefore provided to produce selective, controlled lesions of the dopamine systems in the midbrain in the regions most commonly antagonized by medications to alleviate positive symptoms of schizophrenia. Dopamine-producing cells are selectively destroyed to a level that ameliorates symptoms of schizophrenia, permanently or long-term, without causing Parkinson's-like symptoms, and without other undesirable side effects. This is accomplished by the administration of neurotoxic 1-methyl-4-phenyl-1,2,3,6-tetrahydropyridine (MPTP) or an effective analog, ion or salt thereof. These compounds attack dopamine-producing neurons, as well as some cells involved in norepinephrine and serotonin uptake. It is necessary to destroy about eighty percent of dopamine-producing neurons before symptoms of Parkinsons occur, as discussed above. So long as dosages are kept below amounts producing this extensive amount of damage, there is little danger of producing motor dysfunctions typical of Parkinson's disease when administering MPTP and related compounds. Reduction of dopamine levels throughout the brain is achieved at these dosages and provides observable amelioration of schizophrenic symptoms.

Furthermore, the treatment of this invention targets only subcortical dopamine neurons, thus it will not induce reductions of dopamine availability in hypofunctional areas of the frontal and temporal lobes that are also antagonized by neuroleptics. Thus, this treatment potentiates a restorative effect on cortical/subcortical circuitry and dopamine function. (See Gray, J. A. [1998], "Integrating Schizophrenia," *Schizophrenia Bull.* 24(2):249–266.)

The treatment permanently reduces positive symptoms of schizophrenia without chronic dopamine receptor antagonism, restoring homeostasis between the hypofunctional cortical areas in relation to the hyperfunctional subcortical areas of the schizophrenic brain. MPTP and related compounds act like high-powered neuroleptics but without the side effects, relapses, and non-compliance of known neuroleptic medications. Given in several controlled doses, they produce the same results which prescribed regimens of neuroleptics are aimed at achieving.

With respect to negative symptoms of schizophrenia which are persistent and stable even following conventional neuroleptic treatment that reduces positive symptoms (Arndt, S. et al. [1995], "A longitudinal study of symptom dimensions in schizophrenia," *Arch. Gen. Psychiatry* 52:352–359), since, as discussed above, neuroleptic medications that potentiate receptor upregulation in the hypofunctional cortical areas also antagonize those dopamine receptors the same way they antagonize the striatal and limbic dopamine receptors, restorative effects of cortical-subcortical circuitry that could alleviate this hypofunctionality is essentially impeded. Neuroleptic-treated individuals who have incurred this upregulation benefit by the procedure of this invention that specifically attenuates dopamine levels in the midbrain region, leading to alleviation of negative symptoms of schizophrenia.

The treatment of this invention using MPTP and related compounds for dopamine reduction reduces regional specific overactivity in the midbrain dopamine system. This also serves to restore some of the deficient frontal metabolic activity, allowing neurochemical messages sent from the higher cortical structures to the midbrain (and vice versa) to be adequately communicated (Gray, J. A. [1998], "Integrating schizophrenia," *Schizophrenia Bull.* 24(2):249–266). As the condition of schizophrenia has previously been treated, such a restoration of neurocircuitry was prevented from occurring. Neuroleptic medications inherently antagonize dopamine receptors both in cortical and subcortical areas, serving to "suppress" psychosis yet also impeding the transmission of dopamine chemical communication between cortical/subcortical areas. Midbrain-specific dopamine attenuation restores communication within these neural circuits, making this treatment much more efficacious than just another psychosis "suppressing" drug.

Since MPTP has both the ability to deplete dopamine like the dopamine depleters used to treat tardive dyskinesias and to restore metabolic activity in the globus pallidus and thalamic areas as discussed above, administration of MPTP provides alleviation of tardive dyskinesias.

Compounds useful in this invention are neurotoxic substrates for monoamine oxidase A and/or B known to the art, preferably those having the following general formula:

I

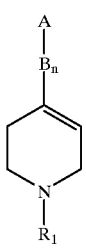

where $R_1$ is H, methyl, $CH_2CCH$, phenyl or benzyl;

A is substituted or unsubstituted phenyl, a substituted or unsubstituted, saturated or unsaturated, five- or six-membered heterocyclic carbon ring having S or O as a ring member, or a substituted or unsubstituted, saturated or unsaturated, five- or six- membered cycloalkyl ring or $N(CH_3)_2$;

n=1 or 0;

B is $CH_2$ or O;

ions thereof having a positively charged nitrogen (pyridinum ions thereof);

or pharmaceutically acceptable salts of the foregoing.

The active form of the compounds of Formula I are metabolites thereof which are pyridinium ions of the formula:

II

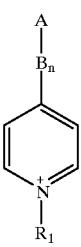

wherein $R_1$, A, B and n are as defined above, and the nitrogen atom bears a positive charge.

A class of preferred pyridinium ions comprises compounds of Formula II in which n is 0, and when A is phenyl, $R_1$ is phenyl, propyl or cyclopropyl; and in which when $R_1$ is methyl, A is cyclohexyl 3-cyclohexenyl, benzyl or $N(CH_3)_2$; and 4' methyl-$MPP^+$.

Another class of preferred pyridinium ions comprises compounds of Formula II in which n is 0, A is phenyl and $R_1$ is $CH_2CCH$ or benzyl. A further class comprises compounds of Formula II in which n is 0, A is tertbutyl and $R_1$ is methyl.

Preferred pyridinium ions include 2'-methyl and 4'-amino $MPP^+$. Another preferred pyridinium ion is 4'-$N(CH_3)_2$-$MPP^+$. A further preferred pyridinium ion is 1-methyl-4-phenylpyridine, the 4-phenyl isomer of $MPP^+$. A further preferred pyridinium ion is 1-methyl-2-phenylpyridine, the 2-phenyl isomer of $MPP^+$.

The MPTP analogs corresponding to the above preferred pyridinium ions form classes of preferred compounds of this invention.

These compounds may be directly administered to the patient. Suitable pharmaceutical salts of these ions may also be administered.

Another preferred class of compounds of this invention are compounds selected from the group consisting of those having the formulae:

III

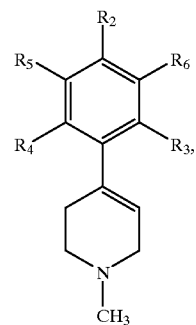

IV

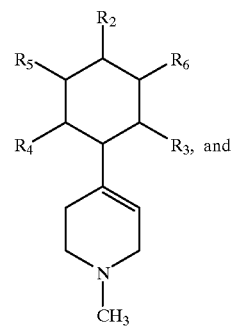

V

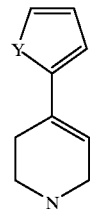

where $R_2$ is H or amino;

$R_3$ and $R_4$ are independently H, $CH_3$, $C_2H_5$, X, or $CX_3$; where X is F, Cl, Br or I;

$R_5$ and $R_6$ are independently H, OH, $OCH_3$ and X; and

Y is S or O;

pyridinium ions thereof, and pharmaceutically acceptable salts of the foregoing.

A further preferred class of compounds are the MPTP analogs 2'-methyl-MPTP, 2'-fluoro-MPTP, 2'-chloro-MPTP, 3'-chloro-MPTP, 3'-bromo-MPTP and 1-methyl-4-t-butyl-1,2,3,6-tetrahydropyridine; pyridinium ions thereof; and pharmaceutically acceptable salts of the foregoing.

Selective neural protective agents may be administered in combination with MPTP, its analogs, ions or salts, to prevent damage to dopaminergic neurons, or neurons other than dopaminergic neurons, e.g., those involved in norepinephrine and serotonin uptake.

In addition, toxicity enhancing agents may be administered in combination with MPTP, its analogs, ions or salts, to prevent axonal growth in dopamine-producing cells.

Dopamine upregulation agents or other antidotes may be administered as part of the treatment method of this invention if indicated after evaluation of the clinical effects of administration of the above compounds.

Pharmaceutical compositions suitable for intravenous administration to human patients comprising MPTP or its analogs, $MPP^+$ or other pyridinium ions of such analogs, or pharmaceutically acceptable salts of the foregoing, in effective dosage amounts, as will be readily ascertainable to those skilled in the art. The term "intravenous administration" includes injection and other modes of intravenous administration.

Pharmaceutical compositions comprising combinations of MPTP, its analogs, pyridinium ions thereof, or pharmaceutical salts thereof, with neural protective agents, or toxicity-enhancing agents, or antidotes including agents that raise dopamine levels, preferably to pre-treatment amounts, and mixtures thereof are also included in this invention. Single dosages suitable for intravenous administration to a human of such compositions containing between about 0.14 and about 35 mg of active composition in a pharmaceutical carrier suitable for intravenous administration to a human are also included in this invention.

The goal of the treatment method of this invention is to eliminate the need for patients to chronically take dopamine receptor blocking medications, thus completely avoiding the side effects which typically lead to noncompliance with treatment regimens. Coupling the administration of compositions of this invention to administration of dopamine level enhancers such as L-Dopa, which can be self-administered when the patient is having a bad day or depressed due to normal fluctuations in dopamine levels, will allow patients to return to normal functioning.

DETAILED DESCRIPTION

In a preferred embodiment, MPTP or MPP+ or a suitable pharmaceutical salt thereof is administered to a patient exhibiting symptoms of schizophrenia. The methods of this invention are particularly suited to the treatment of patients with positive symptoms of schizophrenia such as hallucinations and delusions; however, symptoms of thought disorder and negative symptoms such as depression and flatness of affect may respond to treatment if the patient is one who has responded well to clozapine, an effective medication for treatment of both positive and negative symptoms of schizophrenia.

The structural formulae for MPTP and MPP+ are as follows:

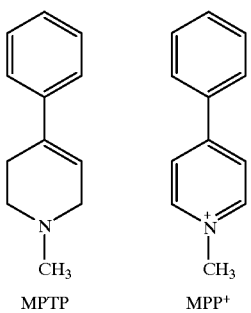

MPTP           MPP+

Analogs of MPTP and MPP+ as described above may also be used in this invention.

MPTP is commercially available, and any analogs which are not commercially available may be prepared by means known to the art. See, e.g. Youngster, S. K. et al. (1987), "Evaluation of the biological activity of several analogs of the dopaminergic neurotoxin 1-methyl-4-phenyl-1,2,3,6-tetrahydropyridine," *J. Neurochem.* 48:929–934; Youngster et al. (1989), "Oxidation of analogs of 1-methyl-4-phenyl-1,2,3,6-tetrahydropyridine by monoamine oxidases A and B and the inhibition of monoamine oxidases by the oxidation products," *J. Neurochem.* 53:1837–1842, both articles being incorporated herein to the extent not inconsistent herewith.

Patients suitable for treatment by means of this invention are preferably patients who have not received previous treatments with dopamine receptor blockers. Intervention as early as possible at onset of the illness could prevent progressive dysfunction of neural circuitry which may occur later in the course of the disease. (Csemansky, J. G. and Bardgett, M. E. [1998], supra.) Patients who have been on long-term treatment with the "typical" $D_2$ blocking neuroleptics such as haloperidol also profit from treatment in accordance with this invention. Depletion of dopamine, which can be accomplished through the methods of this invention, results in alleviation of symptoms of tardive dyskinesias resulting from long-term use of "typical" blocking neuroleptics such as haloperidol. (Egan, F. E. et al. [1997], "Treatment of Tardive Dyskinesia," *Schizophrenia Bull.* 23(4):583–609). Patients who have been treated with "atypical" blocking neuroleptics such as clozapine also benefit from treatment. Patients who show good response to such "atypical" neuroleptics but tend to be noncompliant with such treatment, or in denial, and/or subject to chronic relapses, are good candidates for the treatments of this invention.

Preferably, the treatment of this invention is administered prior to the third or fourth schizophrenic episode. Long-term effects of schizophrenia have been described as resulting in plasticity changes in neural functioning patterns which create abnormalities in the dopaminergic and other neurochemical systems (Lieberman, J. A. et al. [1997], "Neurochemical sensitization in the pathophysiology of schizophrenia deficits and dysfunction in neuronal regulation and plasticity," *Neuropsychopharmacology* 17(4):205–229). By interrupting the dopamine neurotransmitter system's further contributions to abnormal plasticity and sensitization, the formation of permanent pathological circuitry is prevented. Weakening this vital link contributing to pathogenesis impedes further pathogenic processes which eventually seem to manifest throughout all regions of the brain, thus tremendously improving the prognosis and outcomes for individuals who show first signs of schizophrenia and, even in some cases, preventing a diagnosis of schizophrenia from becoming a permanent part of their existence.

Therapeutically effective amounts of the pharmaceutical compositions of this invention can be determined according to methods well-known to the art. The compositions should be given in an amount sufficient to destroy dopamine-producing cells in the brain such that dopamine production is diminished enough to cause a clinically observable change in the symptoms being treated. However, the compositions should not be administered in such large amounts as to cause symptoms of Parkinson's disease such as motor impairment, rigidity or tremor. For example, suitable total dosage amounts of between about 0.001 mg/kg and about 0.5 mg/kg are generally effective, or typically between about 0.01 and about 0.2 mg/kg, depending on the severity of symptoms, prior history of neuroleptic treatment, patient dopamine levels and other factors which are taken into account by those skilled in the art. The dosages requires can be quite variable from patient to patient. Patients may vary as to amounts of dopamine receptors, for example as a result of long-term neuroleptic treatment, and assays to determine the level of receptors may be used in calculating required dosages. The active neurotoxic compositions in suitable pharmaceutical carriers are included in this invention. These total dosage amounts are preferably split into two to five fractional doses for administration in several doses, e.g.

about two to five doses spaced about one to five days apart. Administration should be slow, preferably taking at least about fifteen minutes for each dose.

Since symptoms of Parkinson's are not observed until about eighty percent of dopamine-producing cells are destroyed, as discussed above, while much less cell destruction is required for observable decreases in dopamine production, there is little danger of accidentally overdosing patients. The treatment should achieve less than about eighty percent reduction in dopamine-producing neurons; and is preferably limited to destruction of less than about forty percent, or more preferably less than about twenty percent of dopamine-producing neurons.

To further minimize the risk of inducing motor disorders, it is preferred that the total dosage be given in timed increments, each dose being between about 2 ng/kg and about 0.25 mg/kg, more preferably between about 0.002 and about 0.1 mg/kg. After the first dose, an interval of one to several days should be allowed to observe symptoms, then a second dose given, followed by a similar observation period. The process may be repeated until symptoms have been maximally alleviated, so long as motor dysfunction does not occur. When symptoms have been satisfactorily ameliorated or completely eliminated, no further dosages need be given. If any symptoms typical of Parkinson's disease occur, further dosages should not be given, and antidotes should be administered as is more thoroughly discussed below.

Clinical evaluation of symptoms of schizophrenia can be done by those skilled in the art using art-known methods including standard tests such as the Brief Psychiatric Rating Scale (BPRS), tests of Latent Inhibition, experienced clinical observation, and patient verification of symptom reduction.

Reduction of dopamine in the subcortical regions does not typically result in substantial compensating production of dopamine receptor cells. Neuroleptic receptor blockade has been shown not to result in overall changes in dopamine receptor mRNA activity in the basal ganglion. Several areas of the basal ganglia actually show a reduction of receptor mRNA activity. Significant increases in dopamine receptor mRNA expression have been observed in the cerebral cortex and temporal lobes. (Damask, S. P. et al. [1996], "Differential effects of clozapine and haloperidol on dopamine receptor mRNA expression in rat striatum and cortex," *Molecular Brain Res*. 41:241–249.) Cortical areas have been reported as hypofunctional in schizophrenic patients. Thus, lesions in dopamine-producing areas will not inherently be compensated for by upregulation of dopamine receptor expression in subcortical regions, but may enhance dopamine effects in cortical areas where they are needed. It has been observed that blockading dopamine receptors in the subcortical areas has greatly upregulated dopamine receptor expression in regions which are hypofunctional in schizophrenic patients, such as the frontal cortex and parietal lobes. If patients do respond to damage to dopamine neurons by compensatory receptor upregulation in subcortical regions, this effect should be eliminated by second or subsequent treatments with the compositions of this invention.

The compositions of this invention may include or be administered in the form of pharmaceutically suitable salts as known to the art, e.g. hydrochloride, hydrobromides, phosphates, nitrates, perchlorates, citrates, lactates, tartrates, maleates, fumarates, tartrates, mesylates, esylates and sulfate salts. Such salts are formed by procedures well known in the art.

The compositions may be administered intravenously, orally, intraperitoneally, or by other means known to the art. Preferably the compositions are administered intravenously. For least risk to norephinephrine and serotonin uptake systems in the body, MPTP may be administered into the central nervous system (CNS) side of the blood-brain barrier, such as by spinal injection, where it is quickly converted to the active pyridinium ion which does not pass back through the blood-brain barrier. Preferably, the active compound is injected on the CNS side of the blood-brain barrier in the form of the pyridinium ion. Systemic injection to the body may also be done, as MPTP readily passes the blood-brain barrier where it is converted to the active metabolite MPP+ which does not pass back through the blood-brain barrier. When this systemic form of administration is done, neural protective agents may be administered in advance, e.g. one-half hour or twenty minutes prior to injection of the active compound, to protect norepinephrine and serotonin uptake systems in the body.

The compositions may be mixed with suitable pharmaceutical carriers or excipients known to the art for the chosen dosage form. Such carriers suitable for intravenous administration of the compositions include sterile aqueous or non-aqueous solutions, suspensions or emulsions. Non-aqueous vehicles include propylene glycol, polyethylene glycol, vegetable oils such as olive oil and corn oil, gelatin and injectable organic esters such as ethyl oleate. Such dosage forms may also contain adjuvants such as preserving, wetting, emulsifying and dispersing agents.

The term "administering" includes all forms of introducing the active compositions of this invention into a patient's body, and includes prescribing or supplying treatment components to patients for self-administration.

Neural-protective agents for administration prior to or with the active neurotoxic compounds of this invention include desipramine, which protects against damage to cells responsive to norepinephrine, and citalopram which protects against damage to cells responsive to serotonin. (Javitch, J. A. et al. [1985], "Parkinsonism-inducing neurotoxin, N-methyl-4-phenyl-1,2,3,6-tetrahydropyridine: Uptake of the metabolite N-methyl-4-phenylpyridine by dopamine neurons explains selective toxicity," *Proc. Nat'l Acad. Sci*. 82:2173–2177.) Preferably the treatment of this invention is performed early in the course of the illness since long-term treatment with neuroleptics such as clozapine can severely block serotonin 5HT-2 receptors. When this has occurred it is important to use serotonin neural protective agents with this treatment.

Other types of neuroprotective agents which may selectively protect dopamine neurons in different parts of the brain, or which can be administered selectively to different parts of the brain, include 7-nitroindazole (7-NI) which selectively protects dopamine neurons in the nigral striatal dopaminergic pathway (Przedborski, S. et al. [1996] "Role of neuronal nitric oxide in 1-methyl-4-phenyl-1,2,3,6-tetrahydropyridine (MPTP)-induced dopaminergic neurotoxicity," *Proc. Nat'l Acad. of Sci*. 93(10):4565–4571), and is administered to compensate for the differential effect of the treatment on the ventral tegmental and nigral striatal areas and make dopamine production in these areas closer to equal. Estrogen similarly protects dopamine-producing neurons in the nigral striatal system. (Dluzen, D. E. et al. [1996], "Estrogen Alters MPTP-Induced Neurotoxicity in Female Mice: Effects on Striatal Dopamine Concentrations and Release," *J. Neurochemistry* 66:658–666.)

Additional neuroprotective agents for dopamine neurons include selegiline (L-(-)-deprenyl and its metabolite L-(-)- desmethylselegiline, and 5-methyl-10,11-dihydro-5H-dibenzo[a,d]cyclohepten-5,10-imine maleate (MK-801), deprenyl and other MAO-A and MAO-B inhibitors (Lamensdorf, I. et al. [1996], "Effect of Long-Term Treatment with Selective Monoamine Oxidase A and B Inhibitors on Dopamine Release from Rat Striatum In Vivo," *J. Neurochemistry*, 67(4):1532–1539), mazindol, nomifensine, and pargyline (Javitch [1985], supra; Langston, J. W. et al.[1984], "Pargyline Prevents MPTP-Induced Parkinsonism in Primates," *Science* 225:1480–1482), which can be administered selectively into areas other than the ventral tegmental areas, such as the cerebral cortex and nigral striatal areas, where protection is desired.

Guanethidine administered in advance of MPTP treatment has a protective effect on peripheral neurons. Administered in doses of about 10 mg/kg subcutaneously once a day three days before administration of MPTP, guanethidine protects peripheral neurons including epinephrine neurons without significantly interfering with reductions in dopamine levels.

The foregoing neural-protective agents for dopamine neurons can also be administered as antidotes to prevent progressive damage to dopamine neurons if adverse effects such as motor dysfunctions are observed after administration of the compositions of this invention.

Such neural protective agents should be administered in a dosage adequate to measurably lessen the toxic effects of MPTP on serotonin and norepinephrine-responsive cells, or on dopamine-producing cells, in amounts as is known to the art or may be readily ascertained by those skilled in the art. For example, dosages of manzidol may be administered in dosages of about 10 mg/kg, preferably about thirty minutes prior to administration of neurotoxic compositions of this invention.

Neurotoxicity enhancement agents include compounds which prevent regeneration of dopamine-producing neurons after they have been inactivated by MPP+ and related compounds. Acetaldehyde (ACE) and diethyldiothiocarbamate (DDC) assist in the retrograde transport of MPP+ from the axon of the neuron (where dopamine is produced) to the cell body. (Umberto, C. [1996], "Pharmacological modulation of regenerative processes in the dopaminergic nigrostriatal pathway: a new therapeutic approach to Parkinson's disease and aging," Italian National Research Council web page [1998] http://www.cnr.it.) ACE is preferred as a relatively non-toxic agent, being the major metabolic product of ethanol metabolism. (Thiele, G. M. et al. [1996], "Long-Term Ethanol Administration Alters the Degradation of Acetaldehyde Adducts by Liver Endothelial Cells," *Hepatology*, 24(3):643–648.) As discussed above, MPTP is more toxic to the nigrostriatal dopaminergic pathway than the mesolimbic which arises in the ventral tegmental area. Treatment with MPTP produces a twofold decrease in the number of dopamine neurons in the substantia nigra compared to that in the ventral tegmental area. However, the mesolimbic pathway is highly implicated in most types of schizophrenic symptoms as shown by the fact that the highly-effective antipsychotic clozapine reduces the number of active dopamine cells in mesolimbic/mesocortical cells in the ventral tegmental area that projects to the limbic system. Since MPTP converted to MPP$^+$ is only about half as toxic to the ventral tegmental area than to the substantia nigra and dopamine lesions in the substantia nigra must be kept below the level of eighty percent cell destruction to avoid producing symptoms of Parkinsons, it may become important that any dopamine cell loss in the ventral tegmental area be preserved, and that these cells not be allowed to regenerate. If repeated MPTP treatments were required, the eighty percent limit on cell destruction to the substantia nigra could be exceeded in order to produce a clinically effective reduction in dopamine producing cells in the ventral tegmental area. Thus, administration of a toxicity-enhancing agent such as ACE or DDC may need to be undertaken concomitantly or shortly in advance of administration of MPTP or other neurotoxic compositions of this invention so as to achieve sufficient lesioning in the mesolimbic area to alleviate symptoms of schizophrenia without causing motor dysfunction.

Such toxicity enhancing agents should be administered in a dosage sufficient to prevent substantial regrowth of dopamine neurons, but not such a high dosage to be substantially toxic to other cells. For example, ACE is effective when administered at a dosage of about 400 mg/kg approximately thirty minutes prior to administration of the neurotoxic compositions of this invention.

To further protect dopamine neurons in the nigral striatum, chloroquine and related antimalarial chloroquine compounds such as hydrochloroquine or chloroquine phosphate, and 4-aminoquinoline analogs, referred to herein as "chloroquine compounds," having a high affinity to neuromelanin as known to the art (See, e.g., Lindquist, N. G. [1973], "Accumulation of Drugs on Melanin," *Acta Radiologica Supplementum* 325:19–43) may be used to bind to and protect dopamine neurons in the nigral striatum from MPTP damage. Intramuscular injection of 4 mg/kg chloroquine daily for a period of 24 days was able to prevent MPTP administered intravenously (0.35 mg/kg daily for four consecutive days) from exerting severe neurodegenerative or Parkinsonian effects in a primate model. (D'Amato, R. J. et al. [1987], "Evidence for neuromelanin involvement in MPTP-induced neurotoxicity," *Nature* 327:324–326.) Dosages in similar ratios to the MPTP administered as may be adjusted by those of skill in the art to substantially prevent striatal lesions while allowing therapeutic lesions in the mesolimbic system to occur should be used.

Striatal lesioning should not be totally prevented, however, as the striatum contributes to the overall production of dopamine. In addition, the auditory pathway in this area, as a source of auditory hallucinations, may be normalized by dopamine reduction in the striatum.

Pharmaceutical compositions comprising MPTP, an analog thereof, a biologically active ion of such compounds, and/or pharmaceutical salts of the foregoing, in combination with neural protective agents and/or toxicity enhancing agents are included within the scope of this invention.

If greater-than-desirable destruction of dopamine-producing cells results from administering the pharmaceutical compositions of this invention, a dopamine level enhancer, dopamine neuron protective agent or axon-regenerating agent may be administered as an antidote to the compositions of this invention to raise dopamine levels. Dopamine level enhancers are known to the art and include L-Dopa, adenosine A (sub 2A) receptor antagonists, selegiline and zolpidem. Such dopamine level enhancers should be administered in a dosage sufficient to restore dopamine levels to those required to alleviate physical and adverse mental symptoms, but not such a high dosage as to counteract the effect of MPTP and lead to the original schizophrenic symptoms, such amounts being known to the art or readily ascertainable by those skilled in the art.

Axonal regeneration agents which may be administered if greater than desirable destruction of dopamine-producing cells results from administering the pharmaceutical compositions of this invention include deprenyl, which has been shown to be able to reverse MPP+-induced dopamine neural lesions by promoting new axonal growth and preventing cell death (Tipton, K. F. and Singer, T. P. [1993], "Advances in our Understanding of the Mechanisms of the Neurotoxicity of MPTP and Related Compounds," *J. Neurochem.* 61(4):1191–1206); and brain-derived neurotrophic factor (BDNF), a member of the neurotrophic factor family, which has been found to increase the survival of dopamine neurons in embryonic mesencephalic culture; (Hung, H.-C. and Lee, E. H. Y. [1996], "The mesolimbic dopaminergic pathway is more resistant than the nigrostriatal dopaminergic pathway to MPTP and MPP- toxicity: role of BDNF gene expression," *Molecular Brain Res.* 41:16–26).

Such axonal regeneration agents should be administered in a dosage sufficient to cause sufficient regeneration of dopamine-producing cells to provide a measurable increase in dopamine levels, but not such a high dosage as to completely counteract the effects of administration of MPTP.

Embryonic grafts may also be used as antidotes to counteract destruction of dopaminergic neurons. (Zuddas, A. et al. [1990], "Specific Reinnervation of Lesioned Mouse Striatum by Grafted Mesencephalic Dopaminergic Neurons," *Eur. J. Neuroscience* 3:72–85; DiPorzio, U. and Zuddas, A. [1992], "Embryonic Dopaminergic Neuron Transplants in MPTP Lesioned Mouse Striatum," *Neurochem. Int.* 20(Suppl.):309S-320S.)

Once elimination of positive, primary, especially psychotic symptoms is achieved and the patient becomes stabilized, a variety of approaches for continued rehabilitation may be more successfully employed. These include, but are not limited to:

1. The treatment of secondary symptoms such as depression, bipolar disorder, or anxiety. The manifestation of these individual illnesses or mental disturbances will be more easily identifiable following the diminishment of primary psychotic symptoms.
2. The protocol established by the Schizophrenia Patient Outcomes Research Team (PORT) Treatment Recommendations, especially recommendations following to symptom elimination (i.e., psychological treatments, family therapy, vocational rehabilitation, etc.) should be offered to further the rehabilitation of these individuals and assist them in maximizing their abilities.
3. In treatment-resistant and/or negative symptomatic forms of this illness, other measures of pharmacological intervention may be more successfully employed following the elimination of primary symptoms. Such treatment include, but are not limited to, the use of:
   a. selective serotonergic receptor antagonizing agents;
   b. muscarinic receptor modulating chemicals;
   c. adrenergic receptor antagonists; and
   d. α7-nicotinic receptor agonists.

These receptors appear to play a secondary role in some schizophrenic symptomology. Selective antagonism to the subclasses of serotonergic receptors (such as in the mechanism of several atypical neuroleptics), seems to facilitate the elimination of symptoms in the more difficult-to-treat forms of this illness. Other receptors have been shown to have modulating effects upon dopamine efflux. All classes of neuroleptics possess dopamine receptor blockading mechanisms to which diminished psychosis is attributed, but these mechanisms also seem to be the root of the more devastating side- effects in these patients. With the elimination of psychosis via the dopamine-reduction procedure described herein, isolation and pharmacological manipulation can be more successfully employed to treat the more subtle manifestations of this illness, without the inherent dopamine receptor antagonizing side-effects.

4. Long-term effects of this illness have been described to result in plasticity changes in neural functioning patterns. Early intervention using the treatment methods of this invention before these changes occur is the most desirable approach. In cases of long-term illness in which this treatment method is used, it is imperative (rather than optional) to follow up with a rehabilitative program including the PORT recommendations and personal psychotherapy.

The dopamine reduction procedure of this invention will give credibility to "deinstitutionalization" policies, stop revolving-door patterns of hospitalization, prevent chronic relapse, eliminate issues of non-compliance (especially non-compliance resulting from symptomology of the illness itself), and give individuals suffering from symptoms of schizophrenia the opportunity to grow toward successful participation in society, pursuit of happiness and financial independence for themselves and their families, not only in the United States but wherever this disease affects individuals and societal systems.

Side effects of the pharmaceutical compositions of this invention other than effects of accidental overdose do not present a problem because continued or repeat administration of the compositions is not expected to be necessary once the desired amelioration of symptoms has been achieved.

EXAMPLE 1

Microdialysis Design

A total of 40 male C57 black mice are used to determine the effects of varying doses of MPTP+ACE on neurotransmitter and metabolite levels in the striatum. Each group has n=10 subjects, with one group receiving ACE only (control) and the remaining three groups receiving injections of MPTP+ACE in 5, 10 and 15 mg/kg per day. The test subjects have a sample drawn each day prior to receiving another ACE or MPTP+ACE injection. Deprenyl, 0.25 mg/kg i.p., is administered following a maximum of five days of MPTP administration to evaluate dopamine repotentiation. Microdialysis probes are implanted to directly take these measures. Stereotaxic surgery is performed under 400 mg/kg i.p. of chloral hydrate anesthetic with metofane supplementation as necessary to maintain surgical plane. Probes are implanted into the striatum using the following coordinates: 0.6 mm rostral, 2.4 mm lateral and 4.7 mm ventral to the bregma suture point (see Giovanni et al. [1994b], "Studies on species sensitivity to the dopaminergic neurotoxin 1-methyl-4-phenyl-1,2,3,6-tetrahydropyridine. Part 2: Central administration of 1-methyl-4-phenylpyridinium," *J. Pharmacology and Exp. Therapeutics* 270:1008–1014). Probes are secured with cyanoacrylate and dental cement to assure their viability throughout the entire experiment.

Once implantation of microdialysis probes has been achieved, animals are exposed to a drug regimen intended to deplete dopamine in the striatum. On day 1 of the experiment, intraperitoneal (i.p.) MPTP in varying doses for each group is administered 10 minutes following the administration of 250 mg/kg ACE. An additional dosage of 250 mg/kg ACE is administered 20 minutes following the MPTP injection. Acetaldehyde has been previously shown to potentate the effects of MPTP utilizing this 10 minute pre/20 minute post MPTP injection (Corsini et al. [1987], "1-methyl-4-phenyl-1,2,3,6-tetrahydropyridine (MPTP)

neurotoxicity in mice is enhanced by ethanol or acetaldehyde," *Life Sciences* 40:827–832). This dosage pattern is utilized in all of the following experiments where MPTP is administered. Group 1 receives 250 mg/kg ACE i.p. followed 10 minutes later by an injection of saline, then 20 minutes later a second 250 mg/kg ACE dose i.p. is given. All experimental groups receive 250 mg/kg ACE 10 minutes prior to and 20 minutes following the administration of MPTP. Group 2 receives 5 mg/kg MPTP, group 3 receives 10 mg/kg MPTP, and group 4 receives 15 mg/kg MPTP. Observations are performed to observe motor effects of injections directly after injection protocol. Twenty-four hours later, samples are drawn from the microdialysis probes to measure levels of the monoamines and their metabolites (see below for specifics). Directly after samples have been drawn, animals receive injections identical to the previous day. This regimen is continued for a maximum of 5 days or until motor symptoms occur and do not resolve 24 hours after injections. If extrapyramidal symptoms do not resolve (see Corsini et al. [1987], supra), animals begin a daily regimen of Deprenyl 0.25 mg/kg i.p. (see Lamensdorf et al. [1996], supra) to repotentiate dopamine levels. Again, samples are taken to track the repotentiation of the dopamine over the next several days. All mice are deeply anesthetized with chloral hydrate (400 mg/kg, i.p.) and decapitated. The brains are dissected to confirm the integrity of probe placement. Data from each specimen is considered valid that meets placement criteria or disregarded from further analysis in the event it does not.

Samples for microdialysis are drawn by a microdialysis pump. Dialysis samples are used to measure dopamine dihydroxyphenylacetic acid (DOPAC), homovanillic acid (HVA), serotonin (5HT) and 5-hydrozyindoleacetic acid (5HIAA) through High Pressure Liquid Chromatography. Values for each of these biochemicals are represented as ng/mg of protein and are corrected for recovery of external standards as previously described by Corsini et al. (1987), supra. From this data, doses and dose regimens that produce a 40%, 50%, 60% and 70% depletion of dopamine are noted and further utilized in the behavioral studies described below.

Daily dose dependent reductions followed by repotentiation levels of dopamine are evaluated on an individual subject basis. Overall dose response patterns for the treatment groups are combined and analysis of variance is used to identify between and within group effects. The data gathered from this experiment provide evidence of daily MPTP dosage/dopamine reduction patterns and demonstrate the repotentiation capacity of deprenyl. Feasibility is demonstrated by the achievement of consecutive MPTP dose-dependent dopamine reductions and significant repotentiation of dopamine levels. These data are then utilized in the behavioral and dye coupling experiments.

EXAMPLE 2

MPTP Behavioral Response and Haloperidol Challenge

Neuroleptics given in therapeutic doses are able to attenuate the conditioned avoidance response (CAR) in mice and rats. Prior research indicates that neuroleptic efficacy begins at a 50% binding rate of dopamine receptors in the brain. (Meltzer, L. T. et al. (1995), "CI-1007, a Dopamine Partial Agonist and Potential Antipsychotic Agent. II. Neurophysiological and Behavioral Effects," Sidman, M. (1953), "Avoidance conditioning with brief shock and no exteroceptive warning signal," *Science* 118:157–158; Heise, G. A. and Boff, E. (1962), "Continuous avoidance as a base-line for measuring behavioral effects of drugs," *Psychopharmacologia* 3:264–282.) Following conditioning, four MPTP treatment groups with 40%, 50%, 60% and 70% dopamine reduction levels (as predetermined by the microdialysis study) are evaluated for attenuated responses in the CAR test using pre/post lesion scores. An additional group given therapeutic amounts of haloperidol are used for comparison. The results show superiority in safety and/or efficacy of MPTP to haloperidol.

Task-Naive mice are trained and tested in a one-way signaled avoidance test. The test uses a chamber with an elevated jump-stand and an electrified grid floor. During each trial a barrier that prevents access to the shelf between trials is retracted, and a buzzer sounds (4 seconds) to signal the arrival of an electric shock (10 seconds). When the floor is electrified the mice learn to jump to the shelf to avoid the shock during the test trials. Intertrial intervals are set at 20 seconds and the mice are given 20 consecutive training trials each session. Several sessions per day are given until each mouse achieves a correct response rate of at least 19 out of 20 trials. Mice are then randomly assigned to one of the five treatment groups.

Four groups of (n=5) mice are exposed to MPTP+ACE injections (as described above) which produce 40%, 50%, 60% and 70% depletion of dopamine levels in the striatum (as determined by the microdialysis study). An additional group (n=5) is administered haloperidol 1 ml/kg i.p., dissolved in lactic acid and pH adjusted to 6.0 with NaOH, in the comparison group. Twenty-four hours after the MPTP+ ACE and haloperidol injection (comparison group), conditioned avoidance response is measured. Once the CAR response has been significantly attenuated in one of the MPTP treatment groups, the animals are administered deprenyl (0.25 mg/kg i.p.) to determine if the CAR response can be restored. Following this task, the MPTP treated animals demonstrating significant attenuation of the CARE response are completely withdrawn from deprenyl, sacrificed by cervical dislocation, and their brains removed and striatal areas analyzed for dopamine levels. All other animals are euthanized according to the protocols established by the University of Colorado Health Sciences Center.

This experiment demonstrates that MPTP-induced dopamine can attenuate the conditioned avoidance response in a similar manner to what is observed with therapeutic doses of haloperidol.

EXAMPLE 3

Neurophysiological Similarities of Dye-coupling in MPTP vs. Neuroleptic Groups

Dye-coupling in mesencephalic regions, specifically in the nucleus accumbens (Nac) observed with the chronic administration of clozapine and haloperidol are evaluated in comparison with dye-coupling in MPTP-treated mice. Neuroleptics exert psychosis-eliminating effects on the dopamine system by the mechanisms of depolarization block (which inhibits dopamine neuron spike discharge) and dopamine receptor antagonism (Chiodo, L. A. and Bunney, B. S. (1983), "Typical and atypical neuroleptics: differential effects of chronic administration on the activity of A9 and A10 midbrain dopaminergic neurons," *J. Neuroscience* 3:1607–1619). This study looks at MPTP-induced dopamine reduction (which is similar to depolarization block) and evaluates if this causes a dye-coupling of neurons in the Nac and/or striatum similar to neuroleptics. Dye-coupling between neurons in the Nac is a plastic phenomenon that can undergo alteration with long-term neuroleptic administration. The increase in coupling in the motor-related caudate-putamen (CPu) seen with haloperidol but not clozapine may be related to the EPS-inducing profile of this drug. Both drugs have a similar effect on electronic coupling in the caudal accumbens shell, which may reflect their therapeutic action in the alleviation of positive schizophrenic symptoms. MPTP treatment is evaluated for the manifestation and/or absence of dye-coupling in comparison to observed patterns manifested by the above neuroleptics (O'Donnell, P. O. and Grace, A. A. (1995), "Different effects of subchronic clozapine and haloperidol on dye-coupling between neurons in the rat striatal complex," Neuroscience 66(4):763–767).

This experiment is a between-group comparison of dye-coupled neurons represented in a non-treated group, two neuroleptic treated groups, and an MPTP+ACE treated group. Similarities in neurophysiological responses of dye-coupling between neuroleptic groups and MPTP treated groups are evaluated. On day 1 of the drug administration phase, the MPTP+ACE group (n=10) is given a dose equivalent to that effective to attenuate the conditioned avoidance (determined above) or to evoke a 70% reduction of striatal dopamine availability (predetermined in the microdialysis study), then free-fed and housed for the duration of 21 days. The haloperidol group (n=10) and clozapine group (n=10) respectively receive 0.50 mg/kg and 15 mg/kg i.p. per day for 21 days immediately preceding the experiment. A control group (n=10) receives a 21 day i.p. injection of saline. On day 22, all groups including n=10 untreated controls are sacrificed.

All mice are deeply anesthetized with chloral hydrate (400 mg/kg, i.p.) before decapitation. Brains are carefully removed and 400 $\mu$m thick sagittal slices containing the nucleus accumbens and dorsal striatum are cut while submerged in ice-cold physiological saline solution (124-mM NaCl, 5 mM KCl, 1.2 mM $KH_2PO_4$, 2.4 mM $CaCd_2$, 1.3 mM $MgSO_4$, 26 mM $NaHCO_3$, 10 mM glucose and saturated with 95%:5% $O_2$, $CO_2$) using a Vibratome. Micropipettes are pulled using a Flaming-Brown P-80/PC microelectrode puller and filled with the fluorescent dye Lucifer Yellow (10% in distilled water). After obtaining stable cell penetration, the dye is injected by applying constant hyperpolarizing current (−1.0 nA), interrupted by 10 ms-duration depolarizing pulses to prevent the tip from clogging. After completion of the experiment, the slices are fixed overnight in 10% buffered formalin, cleared in DMSO and later observed under an epifluorescence microscope (Leitz Orthoplan 2).

Slices containing both regions of the nucleus accumbens and the caudate-putamen (CPu) are obtained from all treatment groups (n=30) in which medium-sized (11–20 $\mu$m diameter) densely spinous neurons are successfully penetrated and labeled by intracellular injections of Lucifer Yellow. Since only medium spiny cells exhibit dye-coupling in the accumbens the analysis is limited to this cell type. Since previous studies have shown rostral vs. caudal differences in the modulation of dye-coupling in the accumbens shell, the results obtained from cells injected in the rostral third of the shell region are analyzed separately from those cells injected in the caudal third of the shell. Dye injections for periods of one minute or longer have been shown to consistently yield neurons with brightly stained stomata, dendrites and axons. Labeling of more than one cell is scored as one case of dye-coupling. The number of injections yielding dye-coupling and the number of injections that labeled only single neurons are determined for the different treatment groups, along with the percent of injected cells showing coupling (see O'Donnell, P. O. and Grace, A. A. [1995], "Different effects of subchronic clozapine and haloperidol on dye-coupling between neurons in the rat striatal complex," Neuroscience 66(4):763–767).

This experiment evaluates MPTP treated mice for the presence of dye-coupling, which is observed and considered an efficacious mechanism resulting from neuroleptic use. This experiment predicts that primates manifest dye-coupling in the accumbens as well. When dye-coupling is not evident at all in the MPTP treated group but the conditioned avoidance response is attenuated, this demonstrates a possibility of reduced EPS profile, similar to that of clozapine, over the classic neuroleptic haloperidol. Dye-coupling changes in all treatment groups is compared to control group values. Further analysis of differences between the neuroleptic groups and MPTP group are evaluated for significance.

Estrogen is known to preserve dopamine neurons from effects of MPTP (Dluzen, D. E. et al. [1996], "Estrogen alters MPTP-induced neurotoxicity in female mice: effects on striatal dopamine concentrations and release," J. Neurochemistry 66(2):658–666). Therefore, only male rodents are used.

EXAMPLE 4

Time/Dose Controllability of Dopamine Reduction Levels

Daily consecutive dose-dependent dopamine reduction parameters within the striatum are evaluated by continued administration of MPTP to non-human primates, in excess of therapeutic levels until extrapyramidal side effects (EPS) can be observed. Following this, an antidotal monoamine oxidase-A (MAO-A) inhibitor, 1-Deprenyl, is evaluated for its efficacy in repotentiating dopamine to pretreatment levels and eliminating motor symptoms. (See Tipton, K. F. and Singer, T. P. (1993), "Advances in our understanding of the mechanisms of the neurotoxicity of MPTP and related compounds," J. Neurochem. 61(4):1191–1206.) Since dosages reported in the literature are based on non-human primate studies and there are individual differences in human and non-human primate susceptibility to MPTP (Ballard, P. A., et al. (1985), "Permanent human parkinsonism due to 1-methyl-4-phenyl-1,2,3,6-tetrahydropyridine (MPTP): seven cases," Neurology 35:949–956; German, D. C., et al. (1988), "1-methyl-4-phenyl-1,2,3,6-tetrahydropyridine-induced Parkinsonian syndrome in macaca fascicularis: which midbrain dopaminergic neurons are lost?" Neuroscience 24(1):161–174), the initial dose is determined by evaluating the dopamine/dopamine receptor abnormalities on a per subject basis utilizing PET scans with radioligands (Tune, L. E., et al. (1993), "Dopamine D2 receptor density estimates in schizophrenia: a positron emission tomography study with 11C-N-Methylspiperone," Psychiatry Res. 49:219–237). Following this, several smaller doses are administered to alleviate any residual symptoms.

For subjects already on neuroleptic medications, these are evaluated for compatibility with MPTP since some neuroleptic medications will not interfere with the effect of MPTP on midbrain dopamine neurons (Fuller, R. W. and Hemrick-Juecke, S. K. (1985), "Effects of amfonelic acid, alpha-methyltyrosine, Ro 4-1284 and haloperidol pretreatment on the depletion of striatal dopamine by 1-methyl-4-phenyl-1, 2,3,6-tetrahydropyridine in mice," Res. Comm. In Chem.

*Path and Pharm.*, 48(1):17–25). As is known (Carpenter, W. T. (1997), "The risk of medication-free research," *Schizophrenia Bull.* 23(1):11–18), withdrawing patients from medications can be problematic. Thus the present treatment is administered in stages, the patient being given several incremental doses over time until a medication-free status can be achieved.

The repotentiation of dopamine to baseline values is not an intended normative part of this treatment. In fact, an intentional increase of dopamine levels to or above pretreatment levels would have a restorative or preserving effect on psychosis. The antidote to MPTP is given primarily to establish that there exists an effective antidotal therapy as an ultimate safeguard available to reverse the procedure.

Deprenyl is again administered to evaluate the restoration of pretreatment behavioral responses.

EXAMPLE 5

Hyperprolactinemia Evaluation

Some neuroleptics with D2 receptor affinity have been known to cause hyperprolactinemia (Hansen, et al. (1997), "Neuroleptic intolerance," *Schizophrenia Bull.* 23(4):567–582). Though MPTP has not been identified as selective for the tuberinfundibular tract pre-and post-MPTP treatment, prolactin levels are evaluated to ensure hyperprolactinemia will not be a factor in MPTP-treated patients.

This invention has been illustrated describing specific compositions and procedures. As will be evident to those skilled in the art, analogous compounds and methods may be substituted for those described herein within the scope of the appended claims.

What is claimed is:

1. A method for ameliorating positive and negative symptoms of schizophrenia and tardive dyskinesia comprising administering to a patient exhibiting such symptoms an effective amount of a compound selected from neurotoxic substrates for monoamine oxidase A or B (MAO- A or B) having the following formula:

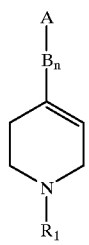

wherein $R_1$ is H methyl, $CH_2CCH$, phenyl or benzyl;

A is substituted or unsubstituted phenyl, a substituted or unsubstituted, saturated or unsaturated five or six-membered heterocyclic ring having S or O as a ring member, a substituted unsubstituted, saturated unsaturated five- six-membered cycloalkyl ring or $N(CH_3)_2$;

n=1 or 0;

B is $CH_2$ or O;

pyridinium ions thereof; and pharmaceutically acceptable salts of the foregoing.

2. A method for ameliorating symptoms of schizophrenia comprising administering to a patient exhibiting such symptoms an effective amount of a compound selected from neurotoxic substrates for monoamine oxidase A or B having the following formulae:

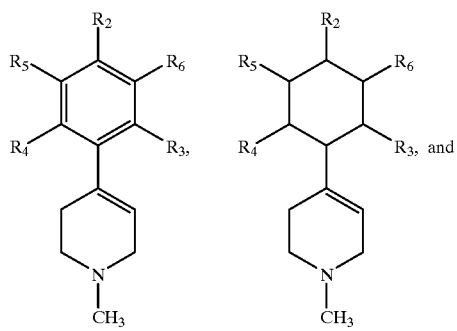

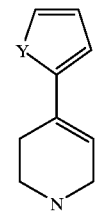

where $R_2$ is H or amino;

$R_3$ and $R_4$ are independently H, $CH_3$, $C_2H_5$, X, or $CX_3$;

where X is F, Cl, Br or I;

$R_5$ and $R_6$ are independently H, OH, $OCH_3$ and X; and N N

Y is S or O;

pyridinium ions thereof; and pharmaceutically acceptable salts of the foregoing.

3. A method of claim 1 comprising administering an effective amount of a neurotoxic pyridinium ion selected from compounds having the following formula:

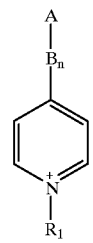

and pharmaceutically effective salts thereof.

4. The method of claim 3 comprising administering a compound in which n is 0 selected from the group consisting of compounds in which when A is phenyl, $R_1$ is phenyl, propyl, cyclopropyl, $CH_2CCH$ or benzyl; compounds in which A is cyclohexyl, 3-cyclohexenyl, benzyl $N(CH_3)_2$ or tert-butyl, and $R_1$ is methyl; and 4'-methyl-1-methyl-4-phenylpyridine (4-methyl-MPP$^+$); and corresponding 1-methyl-4-phenyl-1,2,3,6-tetrahydropyridine (MPTP) analogs.

5. A method for ameliorating positive and negative symptoms of schizophrenia and tardive dyskinesia comprising administering to a patient exhibiting such symptoms an effective amount of a neurotoxic pyridinium ion selected from the group consisting of 2'-methyl MPP$^+$; 4'-amino MPP$^+$; 4'-N(CH$_3$)$_2$-MPP$^+$; the 1-methyl-2-phenylpyridine and 1-methyl-4-phenylpyridine.

6. A method of claim 1 comprising administering a compound selected from the group consisting of 1-methyl-4-phenyl-1,2,3,6-tetrahydropyridine (MPTP); 2'-methyl- MPTP, 2'-fluoro-MPTP, 2'-chloro-MPTP, 3'-chloro-MPTP, 3'-bromo-MPTP and 1-methyl-4-t-butyl-1,2,3,6-tetrahydropyridine; pyridinium ions thereof; and pharmaceutically acceptable salts of the foregoing.

7. The method of claim 1 comprising administering MPTP, 1-methyl-4-phenylpyridinium ion ($MPP^+$) or a pharmaceutical salt of either.

8. The method of claim 1 wherein said administration is intravenous.

9. The method of claim 1 wherein said compound, ion or salt is administered by injection into the central nervous system (CNS) side of the blood-brain barrier.

10. The method of claim 1 wherein said compound, ion or salt is administered by systemic intravenous administration.

11. The method of claim 1 wherein said compound, ion or salt is administered in a total amount between about 0.001 and about 0.5 mg/kg.

12. The method of claim 11 wherein said compound, ion or salt is administered in a sequence of timed doses no greater than about 0.25 mg/kg each.

13. The method of claim 1 wherein said compound, ion or salt is administered in combination with a selective neural protective agent.

14. The method of claim 13 wherein said selective neural protective agent is a serotonin reuptake inhibitor or norepinephrine reuptake inhibitor, or a dopamine neuron protective agent.

15. The method of claim 13 wherein said selective neural protective agent is selected from the group consisting of guanethidine, chloroquine compounds having high affinity to neuromelanin, desipramine, citalopram, 7-nitroindazole (7-NI), estrogen, selegiline (L-(−)-deprenyl) L-(−)-desmethylselegiline, 5-methyl-10,11-dihydro-5H-dibenzo[a,d]cyclohepten-5,10-imine maleate (MK-801), deprenyl, and other MAO-A and MAO-B inhibitors.

16. The method of claim 1 wherein said compound, ion or salt is administered in combination with a toxicity enhancing agent.

17. The method of claim 16 wherein said toxicity enhancing agent is acetaldehyde (ACE) or diethyldithiocarbamate (DDC).

18. The method of claim 1 also comprising evaluating the clinical effects of administration of said compound, ion, or salt and administering a dopamine level enhancer or other antidote.

19. The method of claim 18 wherein said dopamine level enhancer is selected from the group consisting of L-Dopa, adenosine A (sub 2A) receptor antagonists, selegiline and zolpidem.

20. The method of claim 1 wherein said symptoms are positive symptoms of schizophrenia.

21. A method for ameliorating positive symptoms of schizophrenia comprising administering to a patient exhibiting such symptoms MPTP or a pharmaceutically acceptable salt thereof in an amount between about 0.001 and about 0.5 mg/kg by systemic intravenous administration.

22. A method for ameliorating positive symptoms of schizophrenia comprising administering to a patient exhibiting such symptoms MPP+ or a pharmaceutically acceptable salt thereof in an amount between about 0.001 and about 0.5 mg/kg by injection into the CNS side of the blood-brain barrier.

23. A pharmaceutical composition for ameliorating positive and negative symptoms of schizophrenia and tardive dyskinesia in patients exhibiting such symptoms comprising a neurotoxic substrate for monoamine oxidase A or B selected from the group consisting of:

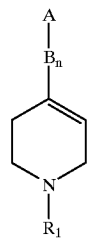

wherein $R_1$ is H methyl, $CH_2CCH$, phenyl or benzyl;

A is substituted or unsubstituted phenyl, a substituted or unsubstituted, saturated or unsaturated five or six-membered heterocyclic ring having S or O as a ring member, a substituted or unsubstituted, saturated or unsaturated five- or six-membered cycloalkyl ring or $N(CH_3)_2$;

n=1 or 0;

B is $CH_2$ or O;

pyridinium ions thereof; and pharmaceutically acceptable salts of the foregoing; and a selective neural protective agent, a toxicity-enhancing agent, or a combination of such agents.

24. A composition of claim 23 wherein said compound, ion, or salt is MPTP, $MPP^+$, or a pharmaceutically acceptable salt thereof.

25. A composition of claim 23 wherein said neural protective agent is selected from the group consisting of desipramine and citalopram, and combinations thereof.

26. A composition of claim 23 wherein said toxicity-enhancing agent is Acetaldehyde (ACE) or diethyldiothiocarbamate (DDC).

27. A dose of a composition of claim 23 comprising an amount between about 0.14 and about 35 mg of said composition in a pharmaceutical carrier suitable for intravenous administration into a human.

28. The composition of claim 23 wherein said compound, ion or salt is MPTP, $MPP^+$, or a pharmaceutically acceptable salt of either.

29. A pharmaceutical composition of claim 23 comprising a neurotoxic pyridinium ion selected from compounds having the following formula:

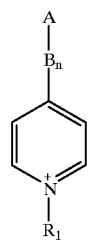

wherein $R_1$, A, B and n are as defined in claim 23, and pharmaceutically effective salts thereof;

and a selective neural protective agent, a toxicity-enhancing agent, or a combination of such agents.

30. A pharmaceutical composition for ameliorating symptoms of schizophrenia in patients comprising a compound selected from the group consisting of neurotoxic substrates for monoamine oxidase A or B having the following formulae:

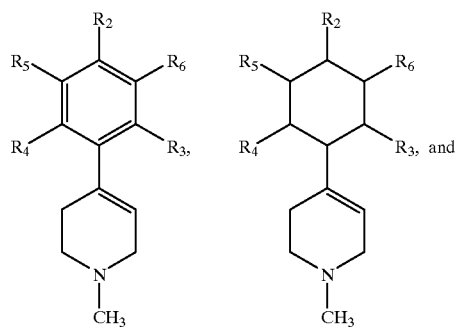

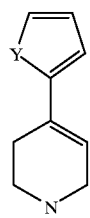

where $R_2$ is H or amino;

$R_3$ and $R_4$ are independently H, $CH_3$, $C_2H_5$, X, or $CX_3$;

where X is F, Cl, Br or I;

$R_5$ and $R_6$ are independently H, OH, $OCH_3$ and X; and

Y is S or O;

pyridinium ions thereof; and pharmaceutically acceptable salts of the foregoing;

and a selective neural protective agent, a toxicity-enhancing agent, or a combination of such agents.

31. A pharmaceutical composition comprising a neurotoxic pyridinium ion selected from the group consisting of 2'-methyl $MPP^+$; 4'-amino $MPP^+$; 4'-$N(CH_3)_2$-$MPP^+$; the 2-phenyl isomer of $MPP^+$; and the 4-phenyl isomer of $MPP^+$ and a selective neural protective agent, a toxicity-enhancing agent, or a combination of such agents.

* * * * *

UNITED STATES PATENT AND TRADEMARK OFFICE
CERTIFICATE OF CORRECTION

PATENT NO. : 6,232,326 B1
DATED : May 15, 2001
INVENTOR(S) : Jodi A. Nelson

It is certified that error appears in the above-identified patent and that said Letters Patent is hereby corrected as shown below:

Column 5,
Line 42, please replace "Relapseinschizophrenia" with -- Relapse in schizophrenia --.

Column 27,
Line 37, please replace "$CaCd_2$" with -- $CaCl_2$ --.

Column 30,
Line 28, in claim 2, four lines below the formulae, please delete "N".
Line 29, in claim 2, five lines below the formulae, please delete "N".

Signed and Sealed this

Thirteenth Day of November, 2001

Attest:

NICHOLAS P. GODICI
Attesting Officer
Acting Director of the United States Patent and Trademark Office